US006197755B1

(12) United States Patent
Carrano et al.

(10) Patent No.: US 6,197,755 B1
(45) Date of Patent: *Mar. 6, 2001

(54) COMPOSITIONS AND METHODS FOR DELIVERY OF GENETIC MATERIAL

(75) Inventors: Richard A. Carrano, Paoli, PA (US); Bin Wang, Haidian (CN); David B. Weiner, Merion, PA (US)

(73) Assignees: The Trustees of the University of Pennsylvania, Philadelphia; Apollan, Inc., Malvern, both of PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/321,461

(22) Filed: May 27, 1999

Related U.S. Application Data

(63) Continuation of application No. 08/704,701, filed as application No. PCT/US95/04071 on Mar. 30, 1995, now Pat. No. 5,962,428, and a continuation of application No. 08/221,579, filed on Apr. 1, 1994, now Pat. No. 5,739,118.

(51) Int. Cl.[7] .................. A61K 31/7088; A61K 45/05
(52) U.S. Cl. .................................. 514/44; 424/278.1
(58) Field of Search .................. 424/93.1, 278.1; 435/69.1, 320.1; 514/44

(56) References Cited

U.S. PATENT DOCUMENTS

| | | | |
|---|---|---|---|
| 4,394,448 | 7/1983 | Szoka, Jr. et al. | 435/458 |
| 4,806,350 | 2/1989 | Gerber | 424/198.1 |
| 4,863,970 | 9/1989 | Patel et al. | 514/784 |
| 4,945,050 | 7/1990 | Sanford et al. | 435/459 |
| 5,023,252 | 6/1991 | Hseih | 514/183 |
| 5,049,386 | 9/1991 | Eppstein et al. | 424/427 |
| 5,084,396 | 1/1992 | Morgan, Jr. et al. | 530/388.8 |
| 5,187,075 | 2/1993 | Green et al. | 435/69.1 |
| 5,273,965 | 12/1993 | Kensil et al. | 514/3 |
| 5,459,127 | 10/1995 | Felgner et al. | 514/7 |
| 5,580,859 | 12/1996 | Felgner et al. | 514/44 |
| 5,593,972 | 1/1997 | Weiner et al. | 514/44 |
| 5,739,118 | 4/1998 | Carrano et al. | 514/44 |
| 5,817,637 | 10/1998 | Weiner et al. | 514/44 |
| 5,830,876 | 11/1998 | Weiner et al. | 514/44 |
| 5,962,428 * | 10/1999 | Carrano et al. | 514/44 |

FOREIGN PATENT DOCUMENTS

| | | |
|---|---|---|
| 2 140822 | 12/1984 | (GB) . |
| WO 86/00930 | 2/1986 | (WO) . |
| WO 96/18372 | 6/1996 | (WO) . |

OTHER PUBLICATIONS

Acsadi et al., "Human Dystrophin Expression in Mdx Mice After Intramuscular Injection of DNA Constructs", *Nature*, 1991, 352, 815–818.

Aida et al., "Removal of Endotoxin from Protein Solutions by Phase Separation using Triton X–114", *J. Immunol. Methods*, 1990, 132, 191–195.

Anilionis et al., "Structure of the Glycoprotein Gene in Rabies Virus", *Nature*, 1981, 294, 275–278.

Bogard et al., "Human Monoclonal Antibody HA–1A Binds to Endotoxin via an Epitope in the Lipid a Domain of Lipopolysaccharide", *J. Immunol.*, 1993, 150, 4438–4449.

Bogerd et al., "Dominant Negative Mutants of Human T–Cell Leukemia Virus Type I Rex and Human Immunodeficiency Virus Type I Rev Fail to Multimerize In Vivo", *J. Virol.*, 1993, 67, 2496–2502.

Bradley, "Virology, Molecular Biology, Serology of Hepatitis C Virus", *Transfusion Medicine Reviews*, 1992, 1, 93–102.

Chaudhary et al., "A Rapid Method of Cloning Functional Variable–Region Antibody Genes in *Escherichia Coli* as Single–Chain Immunotoxins", *Proc. Natl. Acad. Sci. USA*, 1990, 87, 1066–1070.

Cohen, J., "Naked DNA Points Way to Vaccines", *Science*, 1993, 259, 1691–1692.

DiFiore et al., "erbB–2 is a Potent Oncogene When Overexpressed in NIH/3T3 Cells", *Science*, 1987, 237, 178–182.

Edelman et al., "The Covalent and Three–Dimensional Structure of Concanavalin A", *Proc. Natl. Acad. Sci. USA*, 1972, 69, 2580–2584.

Edgington, "Ribozymes Stop Making Sense", *Biotechnology*, 1992, 10, 256–262.

Felgner and Rhodes, "Gene Therapeutics", *Nature*, 1991, 349, 351–352.

Fisher et al., "A Molecular Clone of HTLV–III with Biological Activity", *Nature*, 1985, 316, 262–265.

Furth, P. et al., "Gene Transfer into Somatic Tissues by Jet Injection", *Analytical Biochem.* 1992, 205, 365–368.

Gennaro, (ed.), *Remington's Pharmaceutical Sciences, 18th Edition*, Mark Publishing Co.: Easton, PA, 1990 (including Chapter 50, "Hormones".).

Hirayama et al., "Removal of Endotoxin from Culture Supernatant of *Bordetella Pertussis* with Animated Poly (γ–methyl L–glutamate) Spherical Beads", *Chem. Pharm. Bull.*, 1992, 40, 2106–2109.

(List continued on next page.)

*Primary Examiner*—Robert A. Schwartzman
(74) *Attorney, Agent, or Firm*—Woodcock Washburn Kurtz Mackiewicz & Norris LLP

(57) ABSTRACT

Methods of introducing genetic material into cells of an individual and compositions and kits for practicing the same are disclosed. The methods comprise the steps of contacting cells of an individual with a genetic vaccine facilitator and administering to the cells, a nucleic acid molecule that is free of retroviral particles. The nucleic acid molecule comprises a nucleotide sequence that encodes a protein that comprises at least one epitope that is identical or substantially similar to an epitope of a pathogen antigen or an antigen associated with a hyperproliferative or autoimmune disease, a protein otherwise missing from the individual due to a missing, non-functional or partially functioning gene, or a protein that produce a therapeutic effect on an individual. Methods of prophylactically and therapeutically immunizing an individual against HIV are disclosed. Pharmaceutical compositions and kits for practicing methods of the present invention are disclosed.

24 Claims, 5 Drawing Sheets

OTHER PUBLICATIONS

Hou and Zaniewski, "Depyrogenation by Endotoxin Removal with Positively Charged Depth Filter Cartridge", *J. Parenter. Sci. Technol.,* 1990, 44, 204–209.

Hou et al., "The Effect of Hydrophobic Interaction on Endotoxin Adsorption by Polymeric Affinity Matrix", *Biochem. Biophys. Acta.,* 1991, 1073, 149–154.

Howell et al., "Limited T–Cell Receptor β–Chain Heterogeneity Among Interleukin 2 Receptor–Positive Synovial T Cells Suggest a Role for Superantigen in Rheumatoid Arthritis", *Proc. Natl. Acad. Sci. USA,* 1991, 88, 10921–10925.

Howley, "Papillomavirinae and Their Replication", *Virology,* Fields (ed.), Ravin Press Ltd., New York, 1990, Ch. 58, 1625–1650.

Hug, P. and Sleight, "Liposomes for the Transformation of Eukaryotic Cells", *Biochimica et Biophysica Acta* 1991, 1097, 1–17.

Issekutz, "Removal of Gram–Negative Endotoxin from Solutions by Affinity Chromatography", *J. Immunol. Methods,* 1983, 61, 275–281.

Keller and Mandl, "The Preparation of Purified Collagenase", *Arch. Biochem. Biophys.,* 1963, 101, 81–87.

Kuppuswamy et al., "Multiple Functional Domains of Tat, the Trans–Activator of HIV–1, Defined by Mutational Analysis", *Nucleic Acids Res.,* 1989, 17, 3551–3561.

Lee et al., "Isolation of cDNA for a Human Granulocyte–Macrophage Colony–Stimulating Factor by Functional Expression in Mammalian Cells", *Proc. Natl. Acad. Sci. USA,* 1985, 82, 4360–4364.

Levy et al., "Induction of Cell Differentiation by Human Immunodeficiency Virus 1 vpr", *Cell,* 1993, 72, 541–550.

McCoy, M. et al., "Human Colong Carcinoma Ki–ras2 Oncogene and Its Corresponding Proto–Oncogene", *Molecular and Cellular Biology,* 1984, 4(8), 1577–1582.

Matsumae et al., "Specific Removal of Endotoxin from Protein Solutions by Immobilized Histidine", *Biotech. Appl. Biochem.,* 1990, 12, 129–140.

Morgenstern et al., "Advanced Mammalian Gene Transfer: High Titre Retroviral Vectors with Multiple Drug Selection Markers and a Complementary Helper–Free Packaging Cell Line", 1990, 18, 3587–3596.

Nabel et al., "Site–Specific Gene Expression in Vivo by Direct Gene Transfer into the Arterial Wall",*Science,* 1990, 249, 1285–1288.

Oksenberg et al., "Limited Heterogeneity of Rearranged T–Cell Receptor Vα Transcripts in Brains in Multiple Sclerosis Patients", *Nature,* 1990, 345, 344–346.

Paliard et al., "Evidence for the Effects of a Superantigen in Rheumatoid Arthritis", *Science,* 1991, 253, 325–329.

Paolella et al., "Nuclease Resistant Ribozymes with High Catalytic Activity", *EMBO,* 1992, 11, 1913–1919.

Radziwill et al., "Mutational Analysis of the Hepatitis B Virus P Gene Product: Domain Structure and Rnase H Activity", *J. Virol.,* 1990, 64, 613–620.

Korber and Myers, "Signature Pattern Analysis: A Method for Assessing Viral Sequence Relatedness", *AIDS Res. Human Retro.,* 1992, 8, 1549–1560.

Di Padova et al. and Rietschel, "A Broadly Cross–Protective Monoclonal Antibody Binding to *Escherichia coli* and Salmonella Lipopolysaccharides", *Infect. Immunity,* 1993, 61, 3863–3872.

Sawada et al., *H. Hyg.,* 1986, 97, 103–114.

Schuitemaker et al., "Proliferation–dependent HIV–1 Infection of Monocytes Occurs During Differentiation into Macrophages", *J. Clin. Invest.,* 1992, 89, 1154–1160.

Seed and Aruffo, "Molecular Cloning of the CD2 Antigen, the T–cell Erythrocyte Receptor, by a Rapid Immunoselection Procedure", *Proc. Natl. Acad. Sci. USA,* 1987, 84, 3365–3369.

Shah and Howley, "Papillomaviruses", *Fields Virology,* Channock et al. (eds.), Raven Press Ltd., 1990, Ch. 59, vol. 2, 1651–1676.

Sharma, "Review: Endoxtoxin Detection and Elimination in Biotechnology", *Biotech. App. Biochem.,* 1986, 8, 5–22.

Sigma Chemical Co., *Biochemicals, Organic Compounds for Research and Diagnostic Reagents Catalog,* 1992, 1670–1699.

Sigma Chemical Co., *Biochemicals, Organic Compounds for Research and Diagnostic Reagents Catalog,* 1994, 1799–1810.

Sumner and Howell, "The Identification of the Hemagglutinin of the Jack Bean with Concanavalin A", *J. Bacteriol.,* 1936, 32, 227–237.

Szala et al., "Molecular Cloning of cDNA for the Carcinoma–Associated Antigen GA733–2", *Proc. Natl. Acad. Sci. USA,* 1990, 87, 3542–3546.

Tani et al., *Biomat. Artif. Cells Immobilization Biotechnol.,* 1992, 20, 457–462.

Terwilliger, *AIDS Res. Reviews,* Koff et al. (eds.), Marcel Dekker, Inc.: New York, 1992, 2, 3–27.

Umeda et al., "Novel Endotoxin Adsorbing Materials, Polymyzin–Sepharose and Polyporous Polyethylene Membrane for Removal of Endotoxin from Dialysis Systems", *Biomat. Artif. Cells Artif. Organs,* 1990, 18, 491–497.

Ulmer, J. et al., "Heterologous Protection Against Influenza by Injection of CNA Encoding a Viral Protein", *Science,* 1993, 259, 1745–1749.

Williams et al., "Restricted Heterogeneity of T Cell Receptor Transcripts in Rheumatoid Synovium", *J. Clin. Invest.,* 1992, 90, 326–333.

Williams et al., "Molecular Diagnosis of *Borrelia Burgdorferi* Infection (Lyme Disease)", *DNA and Cell. Biol.,* 1992, 11, 207–213.

Wolfe et al., "Conditions Affecting Direct Gene Transfer Into Rodent Muscle in Vivo", *BioTechniques,* 1991, 11, 474–485.

Wolff et al., "Direct Gene Transfer into Mouse Muscle in Vivo", *Science,* 1990, 247, 1465–1468.

Wucherpfennig et al., "Shared Human T Cell Receptor $V_\beta$ Usage to Immunodominant Regions of Myeline Basic Protein", *Science,* 1990, 248, 1016–1019.

Reddy et al., "Molecular Cloning of Human T–Cell Lymphotrophic Virus Type I–like Proviral Genome from the Peripheral Lymphocyte DNA of a Patient with Chronic Neurologic Disorders", *Proc. Natl. Acad. Sci. USA,* 1988, 85, 3599–3603.

Brown, D., "Gene Therapy 'Oversold' by Researchers, Journalists: NIH Advisers Cite Nearly Uniform Failure", *Wash. Post.,* 1995, A1 and A22.

Coghlan, A., "Gene dream fades away", *New Scientist,* 1995, 148, 14–15.

James, S. et al., "The Influence of Adjuvant on induction of Protective Immunity by a Non–Living Vaccine Against Schistosomiasis", *J. Immunology,* 1988, 140(8), 2753–2759.

Kumar, S. et al., "Immunization of Mice against *Plasmodium vinckei* with a Combination of Attenuated *Salmonella typhimurium* and Malarial Antigen," *Infection and Immunity,* 1990, 58(10), 3425–3429.

Marciani, D. et al., "Genetically–engineered subunit vaccine against feline leukaemia virus: protective immune response in cats", *Vaccine,* 1991, 9, 89–96.

Milligan, J. et al., "Current Concepts in Antisense Drug Design", *J. Med. Chem.,* 1993, 36(14), 1923–1937.

Mulligan, R., "The Basic Science of Gene Therapy", *Science,* 1993, 260, 926–932.

Scott, M. et al., "The vaccine potential of cell surface glycoproteins from *Trypanosoma cruzi*", *Phil. Trans. R. Soc. Lond. B,* 1984, 307, 63–72.

Sigma Chemical Co., *Biochemicals, Organic Compounds for Research and Diagnostic Reagents Catalog,* 1992, 896.

Stein, C. et al., "Antisense Oligonucleotides as Therapeutic Agents—Is the Bullet Really Magical?", *Science,* 1993, 261, 1004–1012.

Tseng, B. et al., "Antisense oligonucleotide technology in the development of cancer therapeutics", *Cancer Gene Therapy,* 1994, 1(1), 65–71.

Uhlmann, E. et al., "Antisense Oligonucleotides: A New Therapeutic Principle", *Chem. Reviews,* 1990, 90(4), 543–584.

Orkin, S. H. et al. "Report and Recommendations of the Panel to Assess the NIH Investment in Research on Gene Therapy", Dec. 7, 1995, 1–40.

Reitz, M.S., "Letter to the Editor on the Historical Origins of HIV–1 (MN) and (RF)", *AIDS Res. Human Retro.,* 1992, 8(9), 1539–1541.

Tolstoshev, P. et al., "Gene Transfer Techniques for Use in Human Gene Therapy," in *Genome Res. Mol. Med. Virol.,* Adolph, K. W. (ed.), Academic Press, San Diego, 1993, Ch. 3, 35–49.

Felgner, J., et al., "Enhanced Gene Delivery and Mechanism Studies with a Novel Series of Cationic Lipid Formulations", *J. Biol. Chem.,* 1994, 269, 2550–2561.

Gao, X. And Huang, L., "A Novel Cationic Liposome Reagent for Efficient Transfection of Mammalian Cells", *Biochem. And Biophys. Res. Commun.,* 1991, 179, 280–285.

Gao, X. And Huang, L., "Cationic liposome–mediated gene transfer", *Gene Therapy,* 1985, 2, 710–722.

Mannino, R. And Gould–Fogerite, S., "Liposome–Mediated Gene Transfer", *Bio/Techniques,* 1988, 6, 682–690.

Nicolau, C., et al., "In vivo expression of rat insulin after intravenous administration the liposome–entrapped gene for rat insulin I", *Medical Sciences,* 1983, 80, 1068–1072.

Philippot, J., et al., "A Very Mild Method Allowing the Encapulation of Very High Amounts of Macromolecules into Very Large (1000nm) Unilamellar Liposomes", *Biochimica et Biophysica Acta,* 1983, 734, 137–143.

Pinnaduwage, P., et al., "User of a quarternary ammonium detergent in liposome mediated DNA transfection of mouse L–cells", *Biochem. et Biophysica Acta,* 1989, 985, 33–37.

Wu, G. and Wu, C., "Receptor–mediated Gene Delivery and Expression in Vivo", *J. Biol. Chem.,* 1988, 263, 14621–14624.

\* cited by examiner

SEQUENCE LISTING (1) GENERAL INFORMATION:

(iii) NUMBER OF SEQUENCES: 48

(2) INFORMATION FOR SEQ ID NO: 1:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 1:

AGGCGTCTCG AGACAGAGGA GAGCAAGAAA TG                                        32

(2) INFORMATION FOR SEQ ID NO: 2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 2:

TTTCCCTCTA GATAAGCCAT CCAATCACAC                                           30

(2) INFORMATION FOR SEQ ID NO: 3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 3:

GAAGGATCCA TGAAAAAATA TTTATTGGG                                            29

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 4:

ACTGTCGACT TATTTTAAAG CGTTTTTAAG                                           30

(2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 5:

GCCAGTTTTG GATCCTTAAA AAAGGCTTGG                                           30

(2) INFORMATION FOR SEQ ID NO: 6:

(i) SEQUENCE CHARACTERISTICS:
        (A) LENGTH: 27 base pairs
        (B) TYPE: nucleic acid (C) STRANDEDNESS: single
        (D) TOPOLOGY: linear (xi) SEQUENCE DESCRIPTION: SEQ ID NO: 6:

TTGTGAGGGA CAGAATTCCA ATCAGGG                                                27

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 7:

CAGTGATATC CCGGGAGACT CCTC                                                   24

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 8:

GAATAGAAGA ACTCCTCTAG AATTC                                                  25

(2) INFORMATION FOR SEQ ID NO: 9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 9:

GCCTTAGGCG GATCCTATGG CAGGAAG                                                27

(2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 10:

TAAGATGGGT GGCCATGGTG AATT                                                   24

(2) INFORMATION FOR SEQ ID NO: 11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 11:

TTGTTTAACT TTTGATCGAT CCATTCC                                                27

(2) INFORMATION FOR SEQ ID NO: 12:

(i) SEQUENCE CHARACTERISTICS:
        (A) LENGTH: 21 base pairs
        (B) TYPE: nucleic acid (C) STRANDEDNESS: single
        (D) TOPOLOGY: linear (xi) SEQUENCE DESCRIPTION: SEQ ID NO: 12:

GATTTGTATC GATGATCTGA C                                             21

(2) INFORMATION FOR SEQ ID NO: 13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 13:

TGTAGTAGCA AAAGAAATAG TTAAG                                         25

(2) INFORMATION FOR SEQ ID NO: 14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 14:

AATTCTTAAC TATTTCTTTT GCTAC                                         25

(2) INFORMATION FOR SEQ ID NO: 15:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 15:

ATTTGTCGAC TGGTTTCAGC CTGCCATGGC AGGAAGAAGC                         40

(2) INFORMATION FOR SEQ ID NO: 16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 16:

ACGACGCGTA TTCTTTAGCT CCTGACTCC                                     29

(2) INFORMATION FOR SEQ ID NO: 17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 17:

GCTGACGGTA GCGGCCGCAC AATT                                          24

(2) INFORMATION FOR SEQ ID NO: 18:

(i) SEQUENCE CHARACTERISTICS:
        (A) LENGTH: 22 base pairs
        (B) TYPE: nucleic acid (C) STRANDEDNESS: single
            (D) TOPOLOGY: linear (xi) SEQUENCE DESCRIPTION: SEQ ID NO: 18:

GTATTAAGCG GCCGCAATTG TT                                                    22

(2) INFORMATION FOR SEQ ID NO: 19:

(i) SEQUENCE CHARACTERISTICS:
            (A) LENGTH: 78 base pairs
            (B) TYPE: nucleic acid
            (C) STRANDEDNESS: single
            (D) TOPOLOGY: linear (xi) SEQUENCE DESCRIPTION: SEQ ID NO: 19:

AAAAAGCTTC GCGGATCCGC GTTGCGGCCG CAACCGGTCA CCGGCGACGC                      50

GTCGGTCGAC CGGTCATGGC TGGGCCCC                                              78

(2) INFORMATION FOR SEQ ID NO: 20:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO: 20:

CCCAAGCTTA GACATGATAA GATACATTG                                             29

(2) INFORMATION FOR SEQ ID NO: 21:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 21:

CTAGCAGCTG GATCCCAGCT TC                                                    22

(2) INFORMATION FOR SEQ ID NO: 22:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 22:

GGATTTCTGG GGATCCAAGC TAGT                                                  24

(2) INFORMATION FOR SEQ ID NO: 23:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO: 23:

TATAGGATCC GCGCAATGAA AGACCCCACC T                                          31

(2) INFORMATION FOR SEQ ID NO: 24:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 24:

ATATGGATCC GCAATGAAAG ACCCCCGCTG A                                       31

(2) INFORMATION FOR SEQ ID NO: 25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 25:

TAAAGCGGCC GCTCCTATGG CAGGAAGACG                                         30

(2) INFORMATION FOR SEQ ID NO: 26:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 26:

ATTACGCGTC TTATGCTTCT AGCCAGGCAC AATG                                    34

(2) INFORMATION FOR SEQ ID NO: 27:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 27:

ATTACGCGTT TATTACAGAA TGGAAAACAG ATGGCAGGTG                              40

(2) INFORMATION FOR SEQ ID NO: 28:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 28:

ATTACGCGTT ATTGCAGAAT TCTTATTATG GC                                      32

(2) INFORMATION FOR SEQ ID NO: 29:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 29:

GAGGCTTGGA GAGGATTATA GAAGTACTGC AAGAGCTG                                38

(2) INFORMATION FOR SEQ ID NO: 30:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 30:

```
GAATCCTCTC CAAGCCTCAG CTACTGCTAT AGCTGTGGC                    39
```

(2) INFORMATION FOR SEQ ID NO: 31:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 31:

```
AAAAATAAAG CGGCCGCTCC TATGGCAGGA AGAGAAGCG                    39
```

(2) INFORMATION FOR SEQ ID NO: 32:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 32:

```
AAAAAATTAC GCGTCTTATG CTTCTAGCCA GGCACAATG                    39
```

(2) INFORMATION FOR SEQ ID NO: 33:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 33:

```
CCCAAGCTTG GGAATGCTCT GCCAGTGTTA C                            31
```

(2) INFORMATION FOR SEQ ID NO: 34:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 34:

```
GGGGGCCGGA AGGGCACAAT AAAACTGTCT GCTTAC                       36
```

(2) INFORMATION FOR SEQ ID NO: 35:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 35:

```
CCTGATTCAG GTGAAAATAT TGTTGATGCG CTG                          33
```

(2) INFORMATION FOR SEQ ID NO: 36:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (xi) SEQUENCE DESCRIPTION: SEQ ID NO: 36:

```
AACATCAATA CAACCTATTA ATTTCCCCTC GTCAAAAATA AGGTTATCAA        50

GTGAGAAATC ACCATCAGTG ACGACTGAAT CCGGTGAGAA TGGCAAAAGT       100

TTATGCATTT C                                                 111
```

(2) INFORMATION FOR SEQ ID NO: 37:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO: 37:

```
CTAGCGCGGG GATCCGCGTT GCGGCCGCAA AAAGTCGACG GGCGACGCGT        50

AAAAA                                                         55
```

(2) INFORMATION FOR SEQ ID NO: 38:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO: 38:

```
GATCTTTTTA CGCGTCGCCC GTCGACTTTT TGCGGCCGCA ACGCGGATCC        50

CCGCG                                                         55
```

(2) INFORMATION FOR SEQ ID NO: 39:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 39:

```
ATGTCGACTG GTTTCAGCCT GCCATGGCAG GAAGAAGC                     38
```

(2) INFORMATION FOR SEQ ID NO: 40:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 40:

```
CCCCACGACG CGTCTATTCT TTAGCTCCTG ACTCC                        35
```

(2) INFORMATION FOR SEQ ID NO: 41:

(i) SEQUENCE CHARACTERISTICS:
        (A) LENGTH: 35 base pairs
        (B) TYPE: nucleic acid (C) STRANDEDNESS: single
        (D) TOPOLOGY: linear (xi) SEQUENCE DESCRIPTION: SEQ ID NO: 41:

TTTGCGGCCG CGTAAGTGGA GAGAGATGGT GCGAG                              35

(2) INFORMATION FOR SEQ ID NO: 42:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 42:

CTGGTGGGGC TGTTGGCTCT G                                            21

(2) INFORMATION FOR SEQ ID NO: 43:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO: 43:

AATTTAATAA GTAAGTAAGT GTCATATGTT TGTTTGAATT CTGCAACAAC              50

TGCTGTTTAT CCATTTTCAG AATTGGGTG                                    79

(2) INFORMATION FOR SEQ ID NO: 44:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO: 44:

TCGACACCCA ATTCTGAAAA TGGATAAACA GCACTTGTTG CAGAATTCAA              50

ACAAACATAT GACACTTACT TACTTATTA                                    79

(2) INFORMATION FOR SEQ ID NO: 45:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 45:

GGGGTTTTTG GCATATGTA TGAGGGACAA TTGGAGAAGT G                       41

(2) INFORMATION FOR SEQ ID NO: 46:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO: 46:

AAGCTTGTGG AATTCTTAAT TTCTCTGTCC GGGGTTTTTG GCATATGTA               50

TGAGGGACAT TGGAGAAGTG                                              70

```
(2) INFORMATION FOR SEQ ID NO: 47:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 47:

CAGTATCTGG CATGGGTAC                                                    19

(2) INFORMATION FOR SEQ ID NO: 48:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 48:

CCATGCCAGA TACTGGTAC                                                    19
```

COMPOSITIONS AND METHODS FOR DELIVERY OF GENETIC MATERIAL

CROSS REFERENCE TO RELATED APPLICATIONS

This application is a continuation of U.S. Ser. No. 08/704,701, filed Sep. 16, 1996, now U.S. Pat. No. 5,962,428, which is the U.S. National Phase of Ser. No. PCT/US95/04071, filed Mar. 30, 1995 and a continuation of U.S. Ser. No. 08/221,579, filed Apr. 1, 1994, which issued on Apr. 14, 1998 as U.S. Pat. No. 5,739,118.

FIELD OF THE INVENTION

The present invention relates to compositions and methods for introducing genetic material into the cells of an individual. The compositions and methods of the invention can be used to deliver protective and/or therapeutic agents including genetic material that encodes protein targets for immunization and therapeutic proteins.

BACKGROUND OF THE INVENTION

The direct introduction of a normal, functional gene into a living animal has been studied as a means for replacing defective genetic information. In some studies, DNA is introduced directly into cells of a living animal without the use of a viral particle or other infectious vector. Nabel, E. G., et al., (1990) *Science* 249:1285–1288, disclose site-specific gene expression in vivo of a beta-galactosidase gene that was transferred directly into the arterial wall in mice. Wolfe, J. A. et al., (1990) *Science* 247:1465–1468, disclose expression of various reporter genes that were directly transferred into mouse muscle in vivo. Acsadi G., et al., (1991) *Nature* 352:815–818, disclose expression of human dystrophin gene in mice after intramuscular injection of DNA constructs. Wolfe, J. A., et al., 1991 *BioTechniques* 11 (4):474–485, which is incorporated herein by reference, refers to conditions affecting direct gene transfer into rodent muscle in vivo. Felgner, P. L. and G. Rhodes, (1991) *Nature* 349:351–352, disclose direct delivery of purified genes in vivo as drugs without the use of retroviruses.

The use of direct gene transfer as an alternative anti-pathogen vaccination method has been suggested. Use of direct gene transfer by single injection is suggested as a possible vaccination strategy against HIV. A cellular immune response to HIV gp120 resulting from introduction of plasmid DNA encoding the same into cells is reported to have been observed. PCT International Application Number PCT/US90/01515 published Oct. 4, 1990 discloses methods of immunizing an individual against pathogen infection by directly injecting naked polynucleotides into the individual's cells in a single step procedure. The use of transfecting agents other than lipofectins is specifically excluded from the disclosed methods. The stimulation of inoculated cells is neither disclosed nor suggested. An HIV vaccine is disclosed which consists of the introduction of polynucleotides that encode the viral protein gp120. The operability of this vaccine is not evidenced.

SUMMARY OF THE INVENTION

The present invention relates to methods of introducing genetic material into the cells of an individual. The methods comprises the steps of contacting cells of said individual with a genetic vaccine facilitator agent and administering to the cells, a nucleic acid molecule that comprises a nucleotide sequence that either encodes a desired peptide or protein, or serves as a template for functional nucleic acid molecules. The genetic vaccine facilitator agent is selected from the group consisting of: anionic lipids; extracellular matrix-active enzymes; saponins; lectins; estrogenic compounds and steroidal hormones; hydroxylated lower alkyls; dimethyl sulfoxide (DMSO); and urea. The nucleic acid molecule is administered free from retroviral particles. The desired protein may either be a protein which functions within the individual or it serves as a target for an immune response.

The present invention relates to a method of immunizing an individual against a pathogen. The method comprises the steps of contacting cells of said individual with a genetic vaccine facilitator agent and administering to the cells, a nucleic acid molecule that comprises a nucleotide sequence that encodes a peptide which comprises at least an epitope identical or substantially similar to an epitope displayed on a pathogen antigen and is operatively linked to regulatory sequences. The nucleic acid molecule is capable of being expressed in the cells of the individual. The genetic vaccine facilitator agent is selected from the group consisting of: anionic lipids; extracellular matrix-active enzymes; saponins; lectins; estrogenic compounds and steroidal hormones; hydroxylated lower alkyls; dimethyl sulfoxide (DMSO); and urea.

The present invention relates to methods of immunizing an individual against a hyperproliferative disease or an autoimmune disease. The methods comprise the steps of contacting cells of said individual with a genetic vaccine facilitator agent and administering to cells of the individual, a nucleic acid molecule that comprises a nucleotide sequence that encodes a peptide that comprises at least an epitope identical or substantially similar to an epitope displayed on a hyperproliferative disease-associated protein or an autoimmune disease-associated protein, respectively, and is operatively linked to regulatory sequences; the nucleic acid molecule being capable of being expressed in the cells. The genetic vaccine facilitator agent is selected from the group consisting of: anionic lipids; extracellular matrix-active enzymes; saponins; lectins; estrogenic compounds and steroidal hormones; hydroxylated lower alkyls; dimethyl sulfoxide (DMSO); and urea.

The present invention relates to methods of treating an individual suffering from an autoimmune disease comprising the steps of contacting cells of said individual with a genetic vaccine facilitator agent and administering to cells of an individual, a nucleic acid molecule that comprises a nucleotide sequence which functions in place of a defective gene or which encodes a molecule that produces a therapeutic effect in the individual and is operatively linked to regulatory sequences; the nucleic acid molecule being capable of being expressed in the cells. The genetic vaccine facilitator agent is selected from the group consisting of: anionic lipids; extracellular matrix-active enzymes; saponins; lectins; estrogenic compounds and steroidal hormones; hydroxylated lower alkyls; dimethyl sulfoxide (DMSO); and urea.

The present invention relates to pharmaceutical compositions which comprise a nucleic acid molecule and a genetic vaccine facilitator. The present invention relates to pharmaceutical kits which comprise a container comprising a nucleic acid molecule and a container comprising a genetic vaccine facilitator. The genetic vaccine facilitator agent is selected from the group consisting of: anionic lipids; extracellular matrix-active enzymes; saponins; lectins; estrogenic compounds and steroidal hormones; hydroxylated lower alkyls; dimethyl sulfoxide (DMSO); and urea.

DETAILED DESCRIPTION OF THE INVENTION

Figure 1:
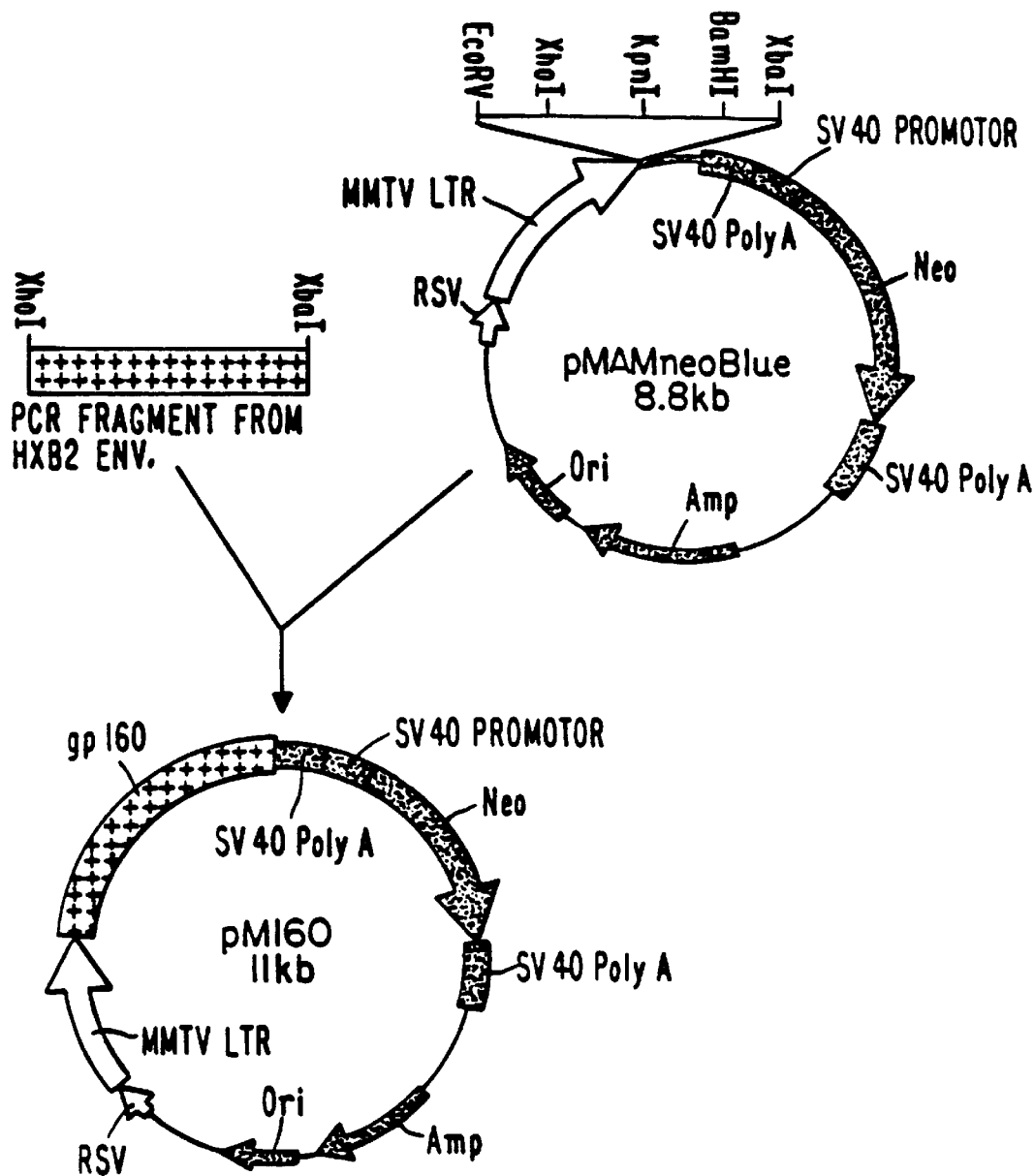
FIG. 1 is a diagram depicting the construction of plasmid pM160 which was produced by inserting a PCR-generated fragment that encodes the HIV-HXB2 glycoprotein gp160 into plasmid pMAMneoBlue (Clonetech).
Figure 2:
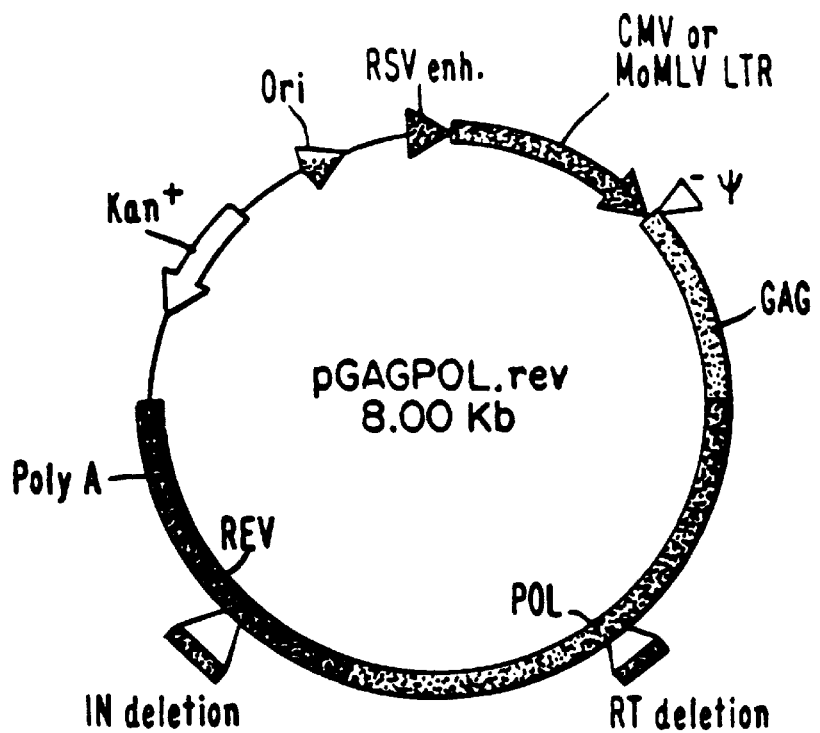
FIG. 2 is a plasmid map of pGAGPOL.rev.
Figure 3:
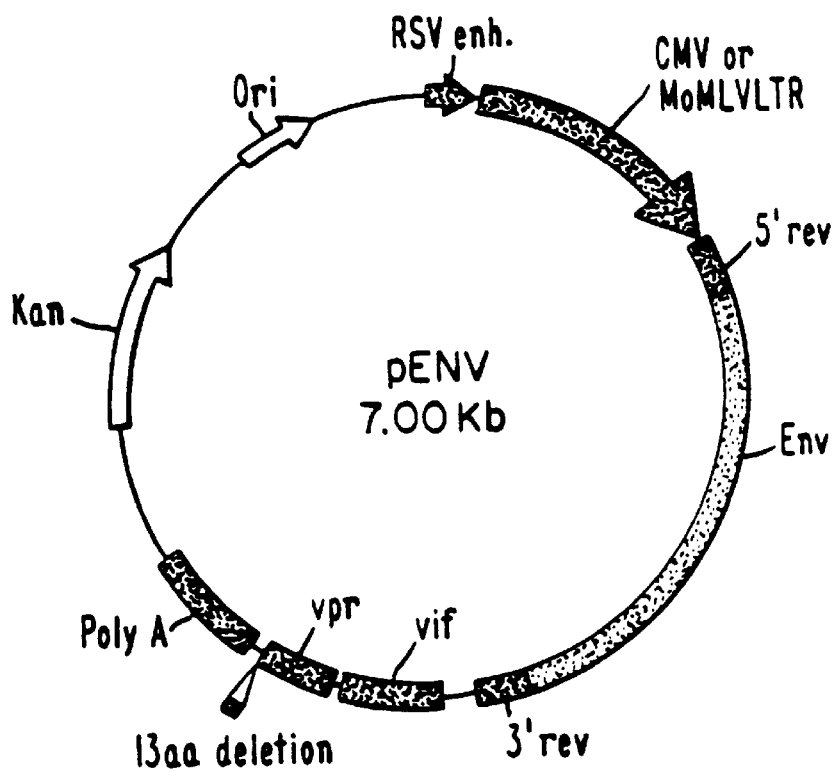
FIG. 3 is a plasmid map of pENV.
Figure 4A:
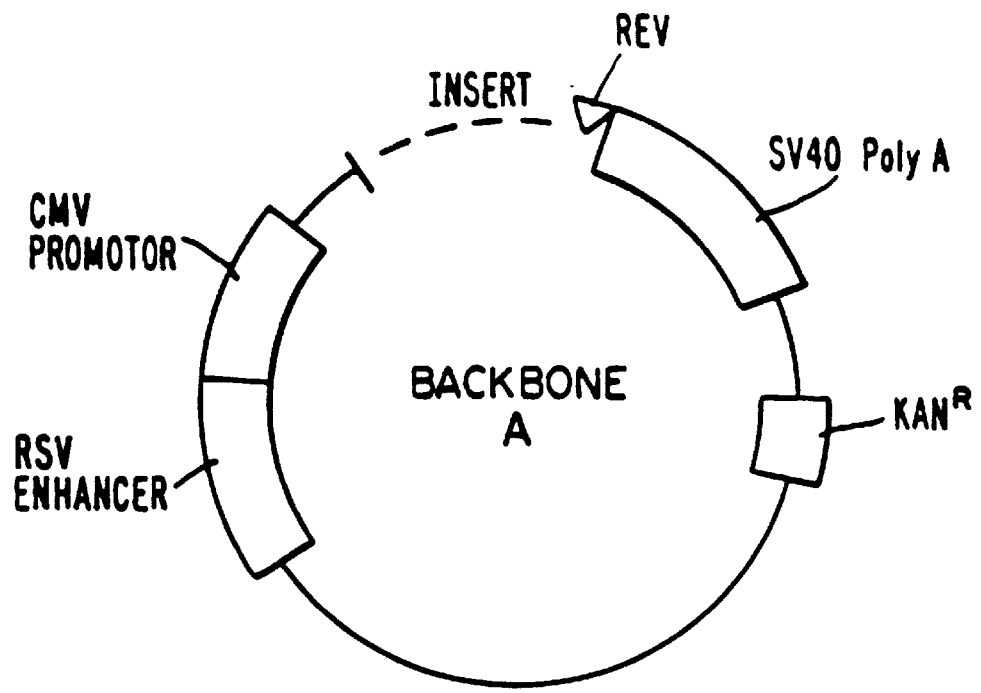
FIGS. 4A–4B show four backbones, A, B, C and D, used to prepare genetic construct.
Figure 4A:
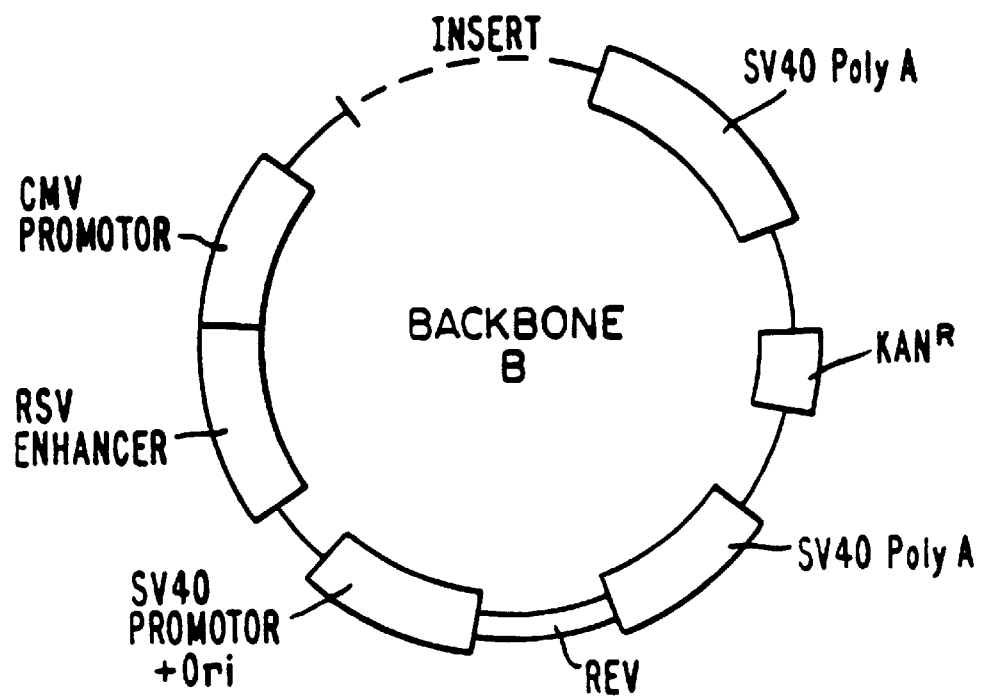
Figure 4B:
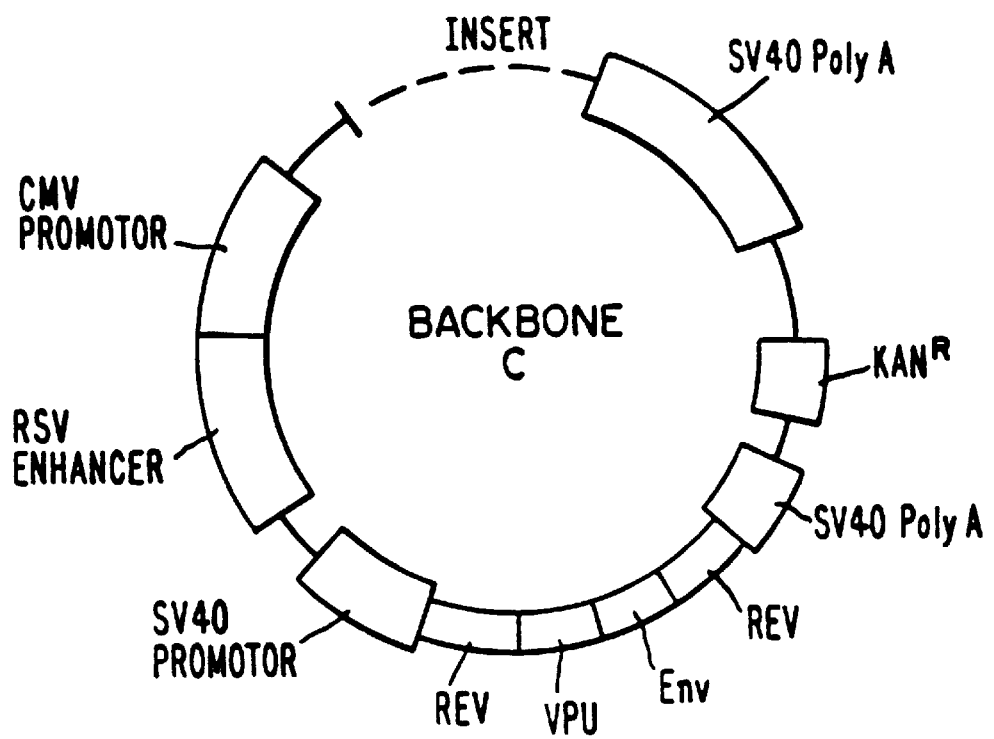
Figure 4B:
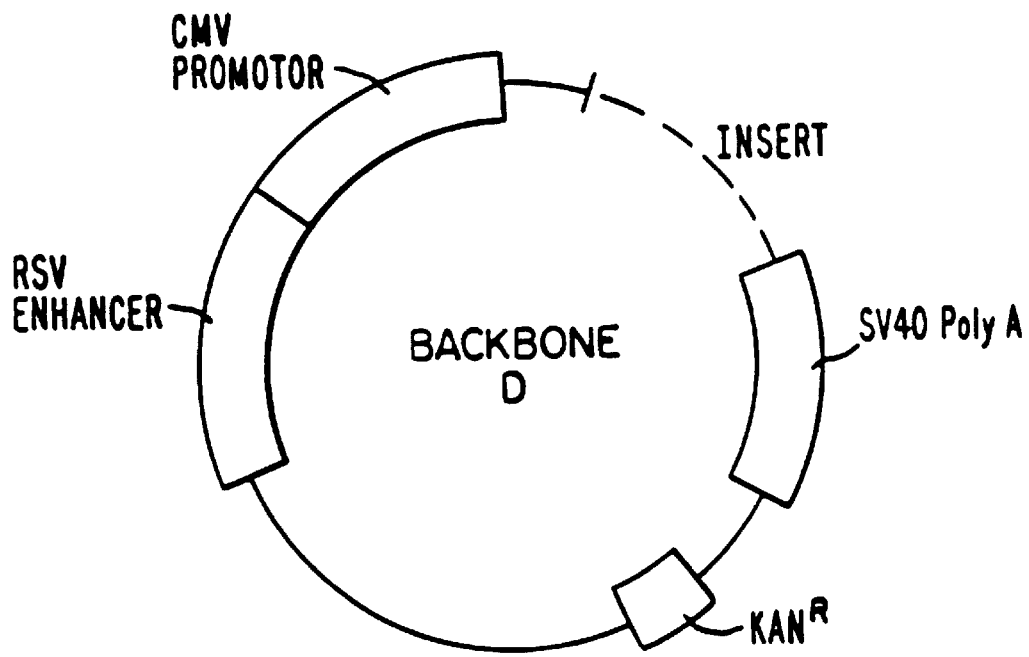
Figure 5:
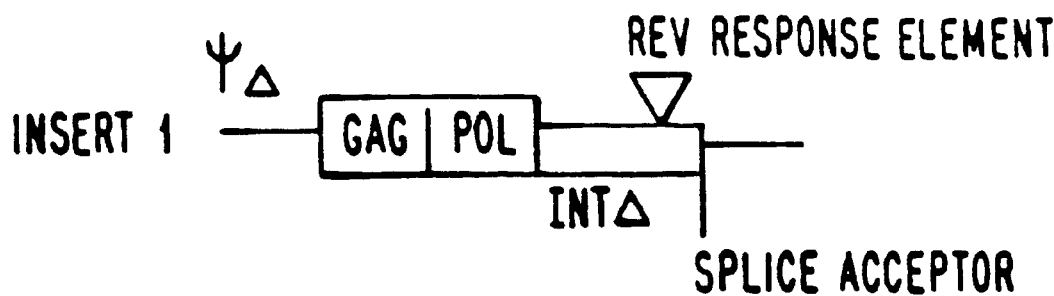
FIG. 5 shows four inserts, 1, 2, 3 and 4 which are inserted into backbones to produce genetic constructs.
Figure 5:
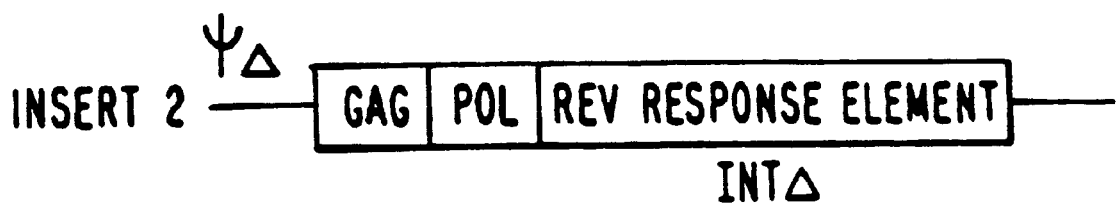
Figure 5:
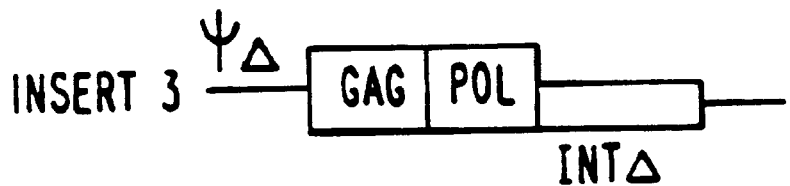
Figure 5:

The present invention relates to a method of introducing nucleic acid molecules into the cells of an animal which provides for the high level of uptake and function of the nucleic acid molecules. The method of the present invention comprises the steps of administering nucleic acid molecules that are free from viral particles, particularly retroviral particles, to the cell of an individual in conjunction with administration of a genetic vaccine facilitator agent. The genetic vaccine facilitator agent is selected from the group consisting of: anionic lipids; extracellular matrix-active enzymes; saponins; lectins; estrogenic compounds and steroidal hormones; hydroxylated lower alkyls; dimethyl sulfoxide (DMSO); and urea. The genetic vaccine facilitator agent preferably enhances the inflammatory response and/or enhances expression of the nucleic acid molecule in the tissue and/or facilitates the uptake of the nucleic acid molecule by the cell. Preferred embodiments of the present invention provide methods of delivering nucleic acid molecules to cells of an individual without the use of infectious agents.

Nucleic acid molecules which are delivered to cells according to the invention may serve as: 1) genetic templates for proteins that function as prophylactic and/or therapeutic immunizing agents; 2) replacement copies of defective, missing or non-functioning genes; 3) genetic templates for therapeutic proteins; 4) genetic templates for antisense molecules; or 5) genetic templates for ribozymes.

In the case of nucleic acid molecules which encode proteins, the nucleic acid molecules preferably comprise the necessary regulatory sequences for transcription and translation in the cells of the animal.

In the case of nucleic acid molecules which serve as templates for antisense molecules and ribozymes, such nucleic acid molecules are preferably linked to regulatory elements necessary for production of sufficient copies of the antisense and ribozyme molecules encoded thereby respectively. The nucleic acid molecules are free from retroviral particles and preferably provided as DNA in the form of plasmids.

The co-agent is also referred to herein as a "genetic vaccine facilitator" or "GVF". As used herein, the term "genetic vaccine facilitator" is meant to refer to co-agents which are administered in conjunction with nucleic acid molecules including genetic vaccines and genetic therapeutics. The GVF is administered as a mixture with the nucleic acid molecule or administered separately simultaneously, before or after administration of nucleic acid molecules. The GVF is used as part of therapeutic or prophylactic methods that include administration of a nucleic acid molecule which encode immunogenic targets, therapeutic proteins, ribozymes or antisense sequences. The GVFs used in the present invention are selected from the group consisting of: anionic lipids; extracellular matrix-active enzymes; saponins; lectins; estrogenic compounds and steroidal hormones; hydroxylated lower alkyls; dimethyl sulfoxide (DMSO); and urea.

According to some aspects of the present invention, compositions and methods are provided which prophylactically and/or therapeutically immunize an individual against a pathogen or abnormal, disease-related cell. The genetic material encodes a peptide or protein that shares at least an epitope with an immunogenic protein found on the pathogen or cells to be targeted. The genetic material is expressed by the individual's cells and serves as an immunogenic target against which an immune response is elicited. The resulting immune response is broad based: in addition to a humoral immune response, both arms of the cellular immune response are elicited. The methods of the present invention are useful for conferring prophylactic and therapeutic immunity. Thus, a method of immunizing includes both methods of protecting an individual from pathogen challenge, or occurrence or proliferation of specific cells as well as methods of treating an individual suffering from pathogen infection, hyperproliferative disease or autoimmune disease.

The present invention is useful to elicit broad immune responses against a target protein, i.e. proteins specifically associated with pathogens or the individual's own "abnormal" cells. The present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

Some aspects of the present invention relate to gene therapy; that is, to compositions for and methods of introducing nucleic acid molecules into the cells of an individual exogenous copies of genes which either correspond to defective, missing, non-functioning or partially functioning genes in the individual or which encode therapeutic proteins, i.e. proteins whose presence in the individual will eliminate a deficiency in the individual and/or whose presence will provide a therapeutic effect on the individual thereby providing a means of delivering the protein by an alternative means from protein administration.

As used herein the term "desired protein" is meant to refer to peptides and protein encoded by gene constructs of the present invention which either act as target proteins for an immune response or as a therapeutic or compensating protein in gene therapy regimens.

According to the present invention, DNA or RNA that encodes a desired protein is introduced into the cells of an individual where it is expressed, thus producing the desired protein. The DNA or RNA encoding the desired protein is linked to regulatory elements necessary for expression in the cells of the individual. Regulatory elements for DNA expression include a promoter and a polyadenylation signal. In addition, other elements, such as a Kozak region, may also be included in the genetic construct.

As used herein, the term "genetic construct" refers to the DNA or RNA molecule that comprises a nucleotide sequence which encodes the desired protein and which includes initiation and termination signals operably linked to regulatory elements including a promoter and polyadenylation signal capable of directing expression in the cells of the vaccinated individual.

As used herein, the term "expressible form" refers to gene constructs which contain the necessary regulatory elements operable linked to a coding sequence that encodes a target protein, such that when present in the cell of the individual, the coding sequence will be expressed.

As used herein, the term "genetic vaccine" refers to a pharmaceutical preparation that comprises a genetic construct that comprises a nucleotide sequence that encodes a target protein including pharmaceutical preparations useful to invoke a therapeutic immune response.

As used herein, the term "genetic therapeutic" refers to a pharmaceutical preparation that comprises a genetic construct that comprises a nucleotide sequence that encodes a therapeutic or compensating protein. Alternatively, a genetic therapeutics may encode antisense sequences which inhibit gene expression of genes whose expression is undesirable. Further, genetic therapeutics may encode ribozymes.

As used herein, the term "target protein" refers to a protein against which an immune response can be elicited. The target protein is an immunogenic protein which shares at least an epitope with a protein from the pathogen or undesirable cell-type such as a cancer cell or a cell involved in autoimmune disease against which immunization is required. The immune response directed against the target protein will protect the individual against and treat the individual for the specific infection or disease with which the target protein is associated.

As used herein, the term "sharing an epitope" refers to proteins which comprise at least one epitope that is identical to or substantially similar to an epitope of another protein.

As used herein, the term "substantially similar epitope" is meant to refer to an epitope that has a structure which is not identical to an epitope of a protein but nonetheless invokes an cellular or humoral immune response which cross reacts to that protein.

As used herein, the term "therapeutic protein" is meant to refer to proteins whose presence confers a therapeutic benefit to the individual.

As used herein, the term "compensating protein" is meant to refer to proteins whose presence compensates for the absence of a fully functioning endogenously produced protein due to an absent, defective, non-functioning or partially functioning endogenous gene.

Genetic constructs comprise a nucleotide sequence that encodes a desired protein operably linked to regulatory elements needed for gene expression. Accordingly, incorporation of the DNA or RNA molecule into a living cell results in the expression of the DNA or RNA encoding the desired protein and thus, production of the desired protein.

When taken up by a cell, the genetic construct which includes the nucleotide sequence encoding the desired protein operably linked to the regulatory elements may remain present in the cell as a functioning extrachromosomal molecule or it may integrate into the cell's chromosomal DNA. DNA may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic construct as a linear minichromosome including a centromere, telomeres and an origin of replication.

The molecule that encodes a desired protein may be DNA or RNA which comprise a nucleotide sequence that encodes the desired protein. These molecules may be cDNA, genomic DNA, synthesized DNA or a hybrid thereof or an RNA molecule such as mRNA. Accordingly, as used herein, the terms "DNA construct", "genetic construct" and "nucleotide sequence" are meant to refer to both DNA and RNA molecules.

The regulatory elements necessary for gene expression of a DNA molecule include: a promoter, an initiation codon, a stop codon, and a polyadenylation signal. In addition, enhancers are often required for gene expression. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments, the vector used is selected form those described in Example 36. In aspects of the invention relating to gene therapy, constructs with origins of replication including the necessary antigen for activation are preferred.

In some preferred embodiments related to immunization applications, the genetic construct contains nucleotide sequences that encode a target protein and further include genes for proteins which enhance the immune response against such target proteins. Examples of such genes are those which encode cytokines and lymphokines such as α-interferon, gamma-interferon, platelet derived growth factor (PDGF), GC-SF, GM-CSF, TNF, epidermal growth factor (EGF), IL-1, IL-2, IL-4, IL-6, IL-8, IL-10 and IL-12. In some embodiments, it is preferred that the gene for GM-CSF is included in genetic constructs used in immunizing compositions.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs which are functional in the cells.

In order to test expression, genetic constructs can be tested for expression levels in vitro using tissue culture of cells of the same type as those to be administered. For example, if the genetic vaccine is to be administered into human muscle cells, muscle cells grown in culture such as solid muscle tumors cells of rhabdomyosarcoma may be used as an in vitro model to measure expression level.

The genetic constructs used in the present invention are not incorporated within retroviral particles. The genetic constructs are taken up by the cell without retroviral particle-mediated insertion such as that which occurs when retrovirus particles with retroviral RNA that is incorporated in retroviral particles infects a cell. As used herein, the term "free from retroviral particles" is meant to refer to genetic constructs that are not incorporated within retroviral particles. As used herein, "dissociated from an infectious agent" is meant to refer to genetic material which is not part of a viral, bacterial or eukaryotic vector, either active, inactivated, living or dead, that is capable of infecting a cell.

In some embodiments, the genetic constructs constitute less than a complete, replicatable viral genome such that upon introduction into the cell, the genetic construct possesses insufficient genetic information to direct production of infectious viral particles. As used herein, the term "incomplete viral genome" is meant to refer to a genetic construct which contains less than a complete genome such that incorporation of such a genetic construct into a cell does not constitute introduction of sufficient genetic information for the production of infectious virus.

In some embodiments, DNA molecules are delivered free from the precipitating agent $CaPO_4$.

In some embodiments, an attenuated viral vaccine may be delivered as a genetic construct which contains enough genetic material to allow for production of viral particles. Delivery of the attenuated vaccine as a genetic construct allows for an easier way to produce large quantities of safe, pure active immunizing product.

The genetic construct may be administered with or without the use microprojectiles. It is preferred that the genetic constructs of the present invention may be delivered to the cells of an individual free of solid particles. As used herein, the phrase "free of solid particles" is meant to refer to a liquid that does not contain any solid microprojectile used as a means to perforate, puncture or otherwise pierce the cell membrane of a cell in order to create a port of entry for genetic material into the cell.

The present invention may be used to immunize an individual against all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhoea, listeria and shigella. In addition, the present invention is also useful to immunize an individual against protozoan pathogens which include a stage in the life cycle where they are intracellular pathogens. As used herein, the term "intracellular pathogen" is meant to refer to a virus or pathogenic organism that, at least part of its reproductive or life cycle, exists within a host cell and therein produces or causes to be produced, pathogen proteins. Table 1 provides a listing of some of the viral families and genera for which vaccines according to the present invention can be made. DNA constructs that comprise DNA sequences which encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2.

In order to produce a genetic vaccine to protect against pathogen infection, genetic material which encodes immunogenic proteins against which a protective immune response can be mounted must be included in the genetic construct. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The genetic construct used in the genetic vaccine can include genetic material which encodes many pathogen antigens. For example, several viral genes may be included in a single construct thereby providing multiple targets. In addition, multiple inoculants which can be delivered to different cells in an individual can be prepared to collectively include, in some cases, a complete or, more preferably, an incomplete such as a near complete set of genes in the vaccine. For example, a complete set of viral genes may be administered using two constructs which each contain a different half of the genome which are administered at different sites. Thus, an immune response may be invoked against each antigen without the risk of an infectious virus being assembled. This allows for the introduction of more than a single antigen target and can eliminate the requirement that protective antigens be identified.

The ease of handling and inexpensive nature of DNA and RNA further allow for more efficient means of screening for protective antigens. Genes can be sorted and systematically tested much more easily than proteins. The pathogenic agents and organism for which the vaccine is being produced to protect against is selected and an immunogenic protein is identified. Tables 1 and 2 include lists of some of the pathogenic agents and organisms for which genetic vaccines can be prepared to protect an individual from infection by them. In some preferred embodiments, the methods of immunizing an individual against a pathogen are directed against HIV, HTLV or HBV.

Another aspect of the present invention provides a method of conferring a broad based protective immune response against hyperproliferating cells that are characteristic in hyperproliferative diseases and to a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis.

It has been discovered that introduction of a genetic construct that includes a nucleotide sequence which encodes an immunogenic "hyperproliferating cell"-associated protein into the cells of an individual results in the production of those proteins in the vaccinated cells of an individual. As used herein, the term "hyperproliferative-associated protein" is meant to refer to proteins that are associated with a hyperproliferative disease. To immunize against hyperproliferative diseases, a genetic construct that includes a nucleotide sequence which encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins which are found at higher levels in tumor cells including the protein recognized by monoclonal antibody 17-1A and folate binding proteins.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include Vβ-3, Vβ-14, Vβ-17 and Vα-17. Thus, vaccination with a DNA construct that encodes at least one of these proteins will elicit an immune response that will target T cells involved in RA. See: Howell, M. D., et al., 1991 *Proc. Natl. Acad. Sci. USA* 88:10921–10925; Paliard, X., et al., 1991 *Science* 253:325–329; Williams, W. V., et al., 1992 *J. Clin. Invest.* 90:326–333; each of which is incorporated herein by reference.

In MS, several specific variable regions of TCRs which are involved in the disease have been characterized. These TCRs include Vβ-7 and Vα-10. Thus, vaccination with a DNA construct that encodes at least one of these proteins will elicit an immune response that will target T cells involved in MS. See: Wucherpfennig, K. W., et al., 1990 *Science* 248:1016–1019; Oksenberg, J. R., et al., 1990 *Nature* 345:344–346; each of which is incorporated herein by reference.

In scleroderma, several specific variable regions of TCRs which are involved in the disease have been characterized. These TCRs include Vβ-6, Vβ-8, Vβ-14 and Vα-16, Vα-3C, Vα-7, Vα-14, Vα-15, Vα-16, Vα-28 and Vα-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 *Sequence of Proteins of Immunological Interest* U.S. Department of Health and Human Services, Bethesda Md., which is incorporated herein by reference. In addition, a general method for cloning functional variable regions from antibodies can be found in Chaudhary, V. K., et al., 1990 *Proc. Natl. Acad. Sci. USA* 87:1066, which is incorporated herein by reference.

In some of the embodiments of the invention that relate to gene therapy, the gene constructs contain either compensating genes or genes that encode therapeutic proteins. Examples of compensating genes include a gene which encodes dystrophin or a functional fragment, a gene to compensate for the defective gene in patients suffering from cystic fibrosis, an insulin, a gene to compensate for the defective gene in patients suffering from ADA, and a gene encoding Factor VIII. Examples of genes encoding therapeutic proteins include genes which encodes erythropoietin, interferon, LDL receptor, GM-CSF, IL-2, IL-4 and TNF. Additionally, genetic constructs which encode single chain antibody components which specifically bind to toxic substances can be administered.

In some preferred embodiments, the dystrophin gene is provided as part of a mini-gene and used to treat individuals suffering from muscular dystrophy. In some preferred embodiments, a mini-gene which contains coding sequence for a partial dystrophin protein is provided. Dystrophin abnormalities are responsible for both the milder Becker's Muscular Dystrophy (BMD) and the severe Duchenne's Muscular Dystrophy (DMD). In BMD dystrophin is made, but it is abnormal in either size and/or amount. The patient is mild to moderately weak. In DMD no protein is made and the patient is wheelchair-bound by age 13 and usually dies by age 20. In some patients, particularly those suffering from BMD, partial dystrophin protein produced by expression of a mini-gene delivered according to the present invention can provide improved muscle function.

In some preferred embodiments, genes encoding IL-2, IL-4, interferon or TNF are delivered to tumor cells which are either present or removed and then reintroduced into an individual. In some embodiments, a gene encoding gamma interferon is administered to an individual suffering from multiple sclerosis.

Antisense molecules and ribozymes may also be delivered to the cells of an individual by introducing genetic material which acts as a template for copies of such active agents. These agents inactivate or otherwise interfere with the expression of genes that encode proteins whose presence is undesirable. Constructs which contain sequences that encode antisense molecules can be used to inhibit or prevent production of proteins within cells. Thus, production proteins such as oncogene products can be eliminated or reduced. Similarly, ribozymes can disrupt gene expression by selectively destroying messenger RNA before it is translated into protein. In some embodiments, cells are treated according to the invention using constructs that encode antisense or ribozymes as part of a therapeutic regimen which involves administration of other therapeutics and procedures. Gene constructs encoding antisense molecules and ribozymes use similar vectors as those which are used when protein production is desired except that the coding sequence does not contain a start codon to initiate translation of RNA into protein. In some embodiments, it is preferred that the vectors described in Example 36, particularly those which contain an origin of replication and expressible form of the appropriate nuclear antigen.

Ribozymes are catalytic RNAs which are capable of self-cleavage or cleavage of another RNA molecule. Several different types of ribozymes, such as hammerhead, hairpin, Tetrahymena group I intron, ahead, and RNase P are known in the art. (S. Edgington, *Biotechnology* 1992 10, 256–262.) Hammerhead ribozymes have a catalytic site which has been mapped to a core of less than 40 nucleotides. Several ribozymes in plant viroids and satellite RNAs share a common secondary structure and certain conserved nucleotides. Although these ribozymes naturally serve as their own substrate, the enzyme domain can be targeted to another RNA substrate through base-pairing with sequences flanking the conserved cleavage site. This ability to custom design ribozymes has allowed them to be used for sequence-specific RNA cleavage (G. Paolella et al., *EMBO* 1992, 1913–1919.) It will therefore be within the scope of one skilled in the art to use different catalytic sequences from various types of ribozymes, such as the hammerhead catalytic sequence and design them in the manner disclosed herein. Ribozymes can be designed against a variety of targets including pathogen nucleotide sequences and oncogenic sequences. Certain preferred embodiments of the invention include sufficient complementarity to specifically target the abl-bcr fusion transcript while maintaining efficiency of the cleavage reaction.

According to some embodiments of the present invention, the genetic construct is administered to an individual using a needleless injection device. According to some embodiments of the present invention, the genetic construct is simultaneously administered to an individual intradermally, subcutaneously and intramuscularly using a needleless injection device. Needleless injection devices are well known and widely available. One having ordinary skill in the art can, following the teachings herein, use needleless injection devices to deliver genetic material to cells of an individual. Needleless injection devices are well suited to deliver genetic material to all tissue. They are particularly useful to deliver genetic material to skin and muscle cells. In some embodiments, a needleless injection device may be used to propel a liquid that contains DNA molecules toward the surface of the individual's skin. The liquid is propelled at a sufficient velocity such that upon impact with the skin the liquid penetrates the surface of the skin, permeates the skin and muscle tissue therebeneath. Thus, the genetic material is simultaneously administered intradermally, subcutaneously and intramuscularly. In some embodiments, a needleless injection device may be used to deliver genetic material to tissue of other organs in order to introduce a nucleic acid molecule to cells of that organ.

According to the invention, the gene constructs may be administered directly into the individual to be immunized or ex vivo into removed cells of the individual which are reimplanted after administration. By either route, the genetic material is introduced into cells which are present in the body of the individual. Routes of administration include, but are not limited to, intramuscular, intraperitoneal, intradermal, subcutaneous, intravenous, intraarterially, intraoccularly and oral as well as transdermally or by inhalation or suppository. Preferred routes of administration include intramuscular, intraperitoneal, intradermal and subcutaneous injection. Delivery of gene constructs which encode target proteins can confer mucosal immunity in individuals immunized by a mode of administration in which the material is presented in tissues associated with mucosal immunity. Thus, in some examples, the gene construct is delivered by administration in the buccal cavity within the mouth of an individual.

Genetic constructs may be administered by means including, but not limited to, traditional syringes, needleless injection devices, or "microprojectile bombardment gene guns". Alternatively, the genetic vaccine may be introduced by various means into cells that are removed from the individual. Such means include, for example, ex vivo transfection, electroporation, microinjection and microprojectile bombardment. After the genetic construct is taken up by the cells, they are reimplanted into the individual. It is contemplated that otherwise non-immunogenic cells that have genetic constructs incorporated therein can be implanted into the individual even if the vaccinated cells were originally taken from another individual.

The genetic vaccines and genetic therapeutics according to the present invention comprise about 1 nanogram to about 1000 micrograms of DNA. In some preferred embodiments, the vaccines and therapeutics contain about 10 nanograms to about 800 micrograms of DNA. In some preferred embodiments, the vaccines and therapeutics contain about 0.1 to about 500 micrograms of DNA. In some preferred embodiments, the vaccines and therapeutics contain about 1 to about 350 micrograms of DNA. In some preferred embodiments, the vaccines and therapeutics contain about 25 to about 250 micrograms of DNA. In some preferred embodiments, the vaccines and therapeutics contain about 100 micrograms DNA.

The genetic vaccines and genetic therapeutics according to the present invention are formulated according to the mode of administration to be used. One having ordinary skill in the art can readily formulate a pharmaceutical composition that comprises a genetic construct. In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are provided sterile and pyrogen free.

The genetic constructs of the invention are formulated with or administered in conjunction with a genetic vaccine facilitator. The GVF increases uptake and/or expression of the genetic construct by the cells compared to that which occurs when the identical genetic vaccine is administered in the absence of the GVF. The GVF is selected from the group consisting of: anionic lipids; extracellular matrix-active enzymes; saponins; lectins; estrogenic compounds and steroidal hormones; hydroxylated lower alkyls; dimethyl sulfoxide (DMSO); and urea. According to some embodiments of the present invention, GVF facilitates uptake of genetic constructs by the cells. According to some embodiments of the present invention, the GVF stimulates cell division and facilitate uptake of genetic constructs. Administration of GVFs that facilitate uptake of genetic constructs by the cells results in a more effective delivery and expression of genetic material. The genetic vaccine facilitator agent preferably facilitates the uptake of DNA by the cells and/or enhances an inflammatory response.

Examples of anionic lipids useful as genetic vaccine facilitators include the salts of lauric and oleic acids, as well as lauric and oleic acids, sulfated alcohols which are neutralized sulfuric acid, acid esters of lauryl and cetyl alcohol, including sodium lauryl sulfate and alkyl polyoxyethylene sulfates. Sulfonates such as dioctyl sodium sulfosuccinate may also be used. The potassium, sodium and ammonium salts of lauric and oleic acids are soluble in water and are good oil/water emulsifying agents. The calcium, magnesium, and aluminum salts of these fatty acids are water insoluble and result in water/oil emulsions. These compounds are pharmaceutical necessities which are widely used in ointments, tooth powders, and various other pharmaceutical preparations as emulsifying agents, detergents, and wetting agents. Examples of such genetic vaccine facilitating agents of the invention are sodium laurate, potassium laurate, sodium lauryl sulfate, potassium lauryl sulfate, ammonium lauryl sulfate, lauric acid, oleic acid, dioctyl sodium sulfosuccinate. Preferred genetic vaccine facilitators are sodium lauryl sulfate and oleic acid.

Sodium Lauryl Sulfate, N.F. (Sodium monododecyl sulfate) is a mixture of sodium alkyl sulfates consisting chiefly of sodium lauryl sulfate which is commercially available for pharmaceutical use (e.g., Duponol®C/DuPont; Gardinol®WA/Proctor & Gamble). It is a highly hydrophilic compound, having a HLB Value (hydrophile/lipophile balance) of 40. Preparations may be formulated for parenteral administration as a genetic vaccine facilitating agent containing 0.1 mg to 100 mg sodium lauryl sulfate per ml, preferably 1 mg to 10 mg, in a pharmaceutically acceptable carrier, preferably sterile water for injection, or sodium chloride injection, or another pharmaceutically acceptable aqueous injection fluid. Other doses and concentrations which achieve the desired facilitation of the effect of the genetic construct may be used. For this application sodium lauryl sulfate is injected into the site of administration of the genetic construct, either before, after, and/or simultaneously, preferably simultaneously, with the administration of the genetic construct.

Oleic acid N.F. consists chiefly of (Z)-9-octadecenoic acid together with variable amounts of other fatty acids such as linolenic and steric acids. Oleic acid preparations may be formulated for parenteral administration as a genetic vaccine facilitating agent containing 0.1 mg to 100 mg oleic acid per ml, preferably 1.0 mg to 10 mg, in a pharmaceutically acceptable carrier, preferably sterile water for injection, or sodium chloride injection, or another pharmaceutically acceptable aqueous injection fluid. Other doses and concentrations which achieve the desired facilitation of the effect of the genetic construct may be used. For this application oleic acid is injected into the site of administration of the genetic construct, either before, after, and/or simultaneously, preferably simultaneously, with the administration of the genetic construct.

Extracellular matrix-active enzymes are hydrolases which catalyze hydrolytic reactions serving to breakdown components of the extracellular matrix surrounding cells in tissues. Examples of extracellular matrix-active enzymes include: collagenase, hyaluronidase, both of which when administered in conjunction with an anti-viral vaccine construct, are administered in conjunction with an incomplete viral genome. In addition, other enzymes which break down structural components in tissue such as amylase and trypsin are contemplated.

Collagenase (clostridiopeptidase A) is a product of clostridium histolyticum. It is a proteolytic enzyme which breaks down native undenatured collagen at physiological pH and temperature. Collagen comprises about 75% of the dry weight of skin. Collagenase may be prepared according to the procedure of Keller et al., 1963 Arch. Biochem. Biophys. 101:81, which is incorporated herein by reference. It is available commercially as an ointment containing 250 units/gram (Santyl®, Knoll). Preparations may be formulated for parenteral administration containing 1.0 to 1000 units collagenase per mL in a pharmaceutically acceptable carrier, e.g., sterile water for injection, sodium chloride injection, or another pharmaceutically acceptable aqueous injection fluid. Other doses and concentrations, e.g., 5.0 to 500 units, preferably 10 to 100 units, which achieve the desired facilitation of the effect of the genetic construct may be used. For this application collagenase is injected into the site of administration of the genetic construct, either before, after, and/or simultaneously, preferably simultaneously, with the administration of the genetic construct.

Hyaluronidase is a mammalian enzyme capable of hydrolyzing mucopolysaccharides of the hyaluronic acid type. Hyaluronidase for injection is available for human pharmaceutical use (Wydase®, Wyeth-Ayerst). Hyaluronidase depolymerizes the hyaluronic acid polymer which serves as the intracellular cement binding together the parenchymal cells of organs, thereby accelerating the subcutaneous spread of both particulate matter and solutions. This results in a larger distribution of drugs in tissue spaces and facilitates their absorption. Absorption is associated with the movement of drug from the site of injection into the vascular system, however, it has now been shown that hyaluronidase also acts as a genetic vaccine facilitator. For this application hyaluronidase is injected into the site of administration of the genetic construct, either before, after, and/or simultaneously, preferably simultaneously, with the administration of the genetic construct. Hyaluronidase for injection is available commercially in dosage forms containing 150 and 1500 units. A dose of 150 units may be dissolved in 1 mL of sodium chloride injection and injected directly, or further diluted with a suitable hypodermoclysis solution, for administration by hypodermoclysis. Other doses and concentrations which achieve the desired facilitation of the effect of the genetic construct may be used, e.g., 100 to 1000 units hyaluronidase per mL, preferably 10 to 100 units/mL, in a pharmaceutically acceptable carrier, e.g., sterile water for injection, or sodium chloride injection, or some other acceptable aqueous injection fluid. For this application, hyaluronidase is injected into the site of administration of the genetic construct, either before, after, and/or simultaneously, preferably simultaneously, with the administration of the genetic construct.

The saponins are a class of glycosides widely distributed in plants. Each saponin consists of a sapogenin which constitutes the aglycone moiety of the molecule, and a sugar. The sapogenin may be a steroid (as in digitonin) or a triterpene (as in aesculin) and the sugar molecule may be glucose, galactose, a pentose, or a methylpentose. Certain saponins have been used as adjuvants to increase the immune response to traditional protein based vaccines. Surprisingly, saponins have now been found to act as genetic vaccine facilitators. A variety of saponins can be used, including natural plant extracts containing a variety of components. Preparations containing saponins may be formulated for parenteral administration containing 0.01 mg to 100 mg per mL in a pharmaceutically acceptable carrier. Other doses and concentrations, e.g., 0.01 mg to 100 mg, preferably 0.1 mg to 10.0 mg per ml., which achieve the desired facilitation of the effect of the genetic construct may be used. For this application the saponin is injected into the site of administration of the genetic construct, either before, after, and/or simultaneously, preferably before administration of the genetic construct.

Included among such useful saponins are various commercially available products prepared from the yucca plant (Saponaria sp.) or from Quillaja species. Preferred are saponins derived from various Saponaria species, e.g., Sigma Chemical Co., Catalog No. S2149.

Examples of commercially available saponins include saponarin and sarmentocymarin. Examples of sapogenins (aglycones) include sarmentogenin, sarsasapogenin, and sarverogenin.

Kensil et al., U.S. Pat. No. 5,273,965, which is incorporated herein by reference, describe various purified and modified saponins useful for delivery of pharmacologically active substances across mucous membranes. The modified saponins exhibit reduced irritability for mucous membranes. Surprisingly, such saponin derivatives can be administered parenterally at the site of administration of the selected genetic construct, either before, after, and/or simultaneously, preferably before administration of the genetic construct.

In some embodiments of the invention, the GVF administered in conjunction with the gene construct is a lectin. The term lectins refers to a group of sugar-binding proteins or glycoproteins of non-immune origin which agglutinate cells and/or precipitate glycoconjugates. Lectins are widely distributed in nature and found primarily in the seeds of plants although they also occur in roots, leaves and bark as well as invertebrates such as clams, snails, horseshoe crabs and several vertebrate species. Lectins are characterized by their ability to agglutinate erythrocytes and many other types of cells. Lectins are described in the SIGMA Chemical Co.'s "Biochemicals, Organic Compounds for Research and Diagnostic Reagents" Catalog appearing at pages 1670–1699 of the 1992 edition, which is incorporated herein by reference, and pages 1799–1810 of the 1994 edition, which is incorporated herein by reference. Examples of lectins includes concanavalin A, abrin, soybean agglutinin and wheat germ agglutinin. In some embodiments, lectins are preferably not glycoproteins; that is, they lack covalently bound carbohydrate.

A preferred non-glycoprotein lectins is concanavalin A (con A) which is commercially available from Sigma Chemical Co. St. Louis Mo. Con A may be isolated from jack bean, Canavalia Ensiformis, Papilionatae (see Sumner, J. B. and S. F. Howell, 1936, J. Bacteriol. 32:227). Con A agglutinates a variety of cell lines through specific interactions with saccharide containing cell surface receptors. Con A has a molecular weight of 27,000 and exists as dimers below pH 6 as a tetrameres physiological pH. The amino acid sequence for Con A is reported in Edelman et al. 1972 *Proc. Natl. Acad. Science USA* 69:2580, which is incorporated herein by reference.

Preparations containing lectins may be formulated for parenteral administration as a genetic vaccine facilitating agent containing 0.1 µg mg to 1.0 mg of a selected lectin per ml, preferably 1.0 µg to 100 µg, in a pharmaceutically acceptable carrier, preferably sterile water for injection, or sodium chloride injection, or another pharmaceutically acceptable aqueous injection fluid. Other doses and concentrations which achieve the desired facilitation of the effect of the genetic construct may be used. For this application, lectin is injected into the site of administration of the genetic construct, either before, after, and/or simultaneously, preferably simultaneously, with the administration of the genetic construct.

Preparations containing conA may be formulated for parenteral administration as a genetic vaccine facilitating agent containing 0.1 µg to 1.0 mg of a conA per ml, preferably 1.0 µg to 100 µg, in a pharmaceutically acceptable carrier, preferably sterile water for injection, or sodium chloride injection, or another pharmaceutically acceptable aqueous injection fluid. Other doses and concentrations which achieve the desired facilitation of the effect of the genetic construct may be used. For this application, conA is injected into the site of administration of the genetic construct, either before, after, and/or simultaneously, preferably simultaneously, with the administration of the genetic construct.

Another group of GVFs include estrogenic compounds and derivatives thereof. Derivative of estrogenic compounds may be steroidal hormones. Preferred steroidal hormones are selected from the group consisting of: β-estradiol and closely related analogs and derivatives thereof.

Both natural and synthetic estrogens may be used. Many compounds are commercially available. Certain nonsteroidal estrogenic compounds such as diethylstilbestrol are more bioavailable and less expensive to synthesize. See e.g., Remington's Pharmaceutical Sciences 18th Edition, Gennaro Ed., Mack Publishing Company, Easton, Pa. 18042 (1990), including Chapter 50, "Hormones".

Estradiol, 17-b-estradiol, (17b)-Estra-1,3,5(10)-triene-3, 17-diol is the most potent natural mammalian estrogenic hormone. Since it is almost insoluble in water, parenteral liquid formulations may utilize pharmaceutically acceptable esters such as estradiol 3-benzoate, estradiol 17b-cypionate, estradiol 17-propionate or dipropionate, hemisuccinate, 17-heptanoate (enanthate), 17-undecanoate (undecylate), 17-valerate. A 0.01% estradiol vaginal cream is available for topical use.

α-estradiol, and esters such as α-estradiol-diacetate or-3-benzoate.

Estriol, Estra-1,3,5(10)-triene-3,16,17-triol, is a less potent estrogenic metabolite of estradiol.

Estrone, 3-hydroxyestra-1,3,5(10)-triene-17-one, and esters such as acetate, propionate, sulfate, sulfate piperazine. Estrone is available as an aqueous suspension containing 20 and 50 mg estrone/10 mL.

Conjugated estrogenic hormones, is a natural product containing water-soluble, conjugated forms of mixed estrogens obtained from the urine of pregnant mares. It is water soluble and is commercially available in a formulation which may be reconstituted to a concentration of 25 mg/5 ml for intravenous or intramuscular injection; and in a vaginal cream containing 0.625 mg conjugated estrogens/gram (Premarin®/Wyeth-Ayerst).

Estrogen congeners such as ethinyl estradiol may also be used.

The desired estrogenic compound(s) may conveniently be selected from a variety of products commercially available for human pharmaceutical use, preferably products in liquid parenteral formulation. To achieve mucosal immunity, e.g., immunity of the vaginal mucosa, a topical formulation such as an estrogen cream or jelly, may be used. Since facilitation of nucleic acid activity at the site of nucleic acid administration rather that systemic estrogenic or other hormonal activity is desired, a dose and concentration that achieves the desired local effect without significant systemic estrogenic or other hormonal activity will preferably be selected. Estrogen preparations may be formulated for parenteral administration as a genetic vaccine facilitating agent containing 0.001 mg/ml to 10 mg/ml estrogenic compound per ml, preferably 0.01 mg/ml to 1.0 mg/ml in a pharmaceutically acceptable carrier, preferably sterile water for injection, or sodium chloride injection, or another pharmaceutically acceptable aqueous injection fluid. Other doses and concentrations which achieve the desired facilitation of the effect of the genetic construct may be used. For this application an estrogenic compound is injected into the site of administration of the genetic construct, either before, after, and/or simultaneously, preferably simultaneously, with the administration of the genetic construct. Optimization of dose/concentration can be achieved using known methodology and routine experimentation by those of skill in pharmacology and the pharmaceutical sciences. A dose and concentration may be administered which provides the desired facilitation of uptake and/or enhancement of expression or immune response to the genetic constructs by cells. The desired estrogenic compound(s) may be administered before, after, and/or simultaneously, preferably simultaneously, with the desired nucleic acid construct.

Hydroxylated lower alkyls have been found to have genetic vaccine facilitating activity. Hydroxylated lower alkyls include ethanol, n-propanol, isopropanol, n-butanol, and glycerol; preferred are ethanol and glycerol.

Ethanol is commercially available for pharmaceutical use; it may be diluted in sterile water for injection, or sodium chloride injection, or other pharmaceutically acceptable injection fluid, and used in concentrations of 0.01 to 100% (v/v), preferably 0.1 to 10% more preferably about 5%, to facilitate the activity of a nucleic acid construct. It may be administered before, after, and/or simultaneously, preferably simultaneously, with the desired nucleic acid construct.

Glycerin or glycerol (1,2,3-propanetriol) is commercially available for pharmaceutical use. It may be diluted in sterile water for injection, or sodium chloride injection, or other pharmaceutically acceptable aqueous injection fluid, and used in concentrations of 0.1 to 100% (v/v), preferably 1.0 to 50% more preferably about 20% v/v, to facilitate the activity of a nucleic acid construct. It may be administered before, after and/or simultaneously, preferably simultaneously, with the desired nucleic acid construct.

Another GVF is DMSO, which is an aprotic solvent with a remarkable ability to enhance penetration of many locally applied drugs. It is approved for instillation into the bladder for the treatment of interstitial cystitis. Applied locally in concentrations above 50%, DMSO breaks down collagen and has anti-inflammatory and local anesthetic effects.

DMSO may be diluted in sterile water for injection, or sodium chloride injection, or other pharmaceutically acceptable aqueous injection fluid, and used in concentrations of 0.1 to 100% (v/v), preferably 1.0 to 50%, more preferably about 20% v/v, to facilitate the activity of a nucleic acid construct. It may be administered, before, after, and/or simultaneously, preferably simultaneously, with the desired nucleic acid construct.

Urea, $H_2NCONH_2$, which is a natural endproduct of protein metabolism which is normally excreted by the kidneys is also a GVF. Two molecules of ammonia react with one molecule of carbon dioxide to form one molecule of water and one molecule of urea. Urea is available commercially for various pharmaceutical uses. Urea is used intravenously as a 30% urea solution in 5 or 10% dextrose solution as an osmotic diuretic to reduce intracranial pressure caused by cerebral edema and to reduce intraocular pressure. It also is used topically for a variety of dermatological applications, including psoriasis, atopic dermatitis, and to remove excess keratin from skin.

Preparations containing urea may be formulated for parenteral administration containing 0.1 to 1000 mg per ml in a pharmaceutically acceptable carrier, such as sodium chloride injection USP, water for injection, USP, 5% dextrose injection, or 10% dextrose injection. Other doses and concentrations, e.g., 1.0 to 100 mg/ml, preferably 60 mg/mL (about 1 M), which achieve the desired facilitation of the effect of the genetic construct may be used. For this application the saponin is injected into the site of administration of the genetic construct, either before, after, and/or simultaneously, preferably before administration of the genetic construct.

In some embodiments of the invention, the individual is first subject to GVF injection prior to genetic vaccination by intramuscular injection. That is, up to, for example, up to a about a week to ten days prior to vaccination, the individual is first injected with a GVF. In some embodiments, prior to vaccination, the individual is injected with a GVF about 1 to 5 days before administration of the genetic construct. In some embodiments, prior to vaccination, the individual is injected with a GVF about 24 hrs before administration of the genetic construct. Alternatively, a GVF can be injected simultaneously, minutes before or after vaccination. Accordingly, the GVF and the genetic construct may be combined and injected simultaneously as a mixture. In some embodiments, the GVF is administered after administration of the genetic construct. For example, up to about a week to ten days after administration of the genetic construct, the individual is injected with GVF. In some embodiments, the individual is injected with a GVF about 24 hrs after vaccination. In some embodiments, the individual is injected with a GVF about 1 to 5 days after vaccination. In some embodiments, the individual is administered a GVF up to about a week to ten days after vaccination.

In some embodiments of the present invention, combinations of GVF agents are administered in conjunction with genetic constructs.

In addition, other agents which may function transfecting agents and/or replicating agents and/or inflammatory agents and which may be co-administered with a GVF include growth factors, cytokines and lymphokines such as α-interferon, gamma-interferon, platelet derived growth factor (PDGF), GC-SF, GM-CSF, TNF, epidermal growth factor (EGF), IL-1, IL-2, IL-4, IL-6, IL-8, IL-10 and IL-12 as well as fibroblast growth factor, surface active agents such as immune-stimulating complexes (ISCOMS), Freund's incomplete adjuvant, LPS analog including monophosphoryl Lipid A (MPL), muramyl peptides, quinone analogs and vesicles such as squalene and squalene, and hyaluronic acid may also be used administered in conjunction with the genetic construct. In some embodiments, combinations of these agents are administered in conjunction with a GVF and the genetic construct.

The genetic construct may be combined with collagen as an emulsion and delivered parenterally. The collagen emulsion provides a means for sustained release of DNA. 50 μl to 2 ml of collagen are used. About 100 μg DNA are combined with 1 ml of collagen in a preferred embodiment using this formulation. Other sustained release formulations such as those described in *Remington's Pharmaceutical Sciences*, A. Osol, a standard reference text in this field, which is incorporated herein by reference. Such formulations include aqueous suspensions, oil solutions and suspensions, emulsions and implants as well as reservoirs and transdermal devices. In some embodiments, time release formulations for genetic constructs are preferred. In some embodiments, it is preferred that the genetic construct is time released between 6–144 hours, preferably 12–96 hours, more preferably 18–72 hours.

In some embodiments of the invention, the genetic construct is injected with a needleless injection device. The needleless injection devices are particularly useful for simultaneous administration of the material intramuscularly, intradermally and subcutaneously.

In some embodiments of the invention, the genetic construct is administered with a GVF by means of a microprojectile particle bombardment procedure as taught by Sanford et al. in U.S. Pat. No. 4,945,050 issued Jul. 31, 1990, which is incorporated herein by reference.

In some embodiments of the invention, the genetic construct is administered as part of a liposome complex with a genetic vaccine facilitator agent.

In some embodiments of the invention, the individual is subject to a single vaccination to produce a full, broad immune response. In some embodiments of the invention, the individual is subject to a series of vaccinations to produce a full, broad immune response. According to some embodiments of the invention, at least two and preferably four to five injections are given over a period of time. The period of time between injections may include from 24 hours apart to two weeks or longer between injections, preferably one week apart. Alternatively, at least two and up to four separate injections are given simultaneously at different sites.

In some embodiments of the invention, a complete vaccination includes injection of a single inoculant which contains a genetic construct including sequences encoding one or more targeted epitopes.

In some embodiments of the invention, a complete vaccination includes injection of two or more different inoculants into different sites. For example, in an HIV vaccine according to the invention, the vaccine comprises two inoculants in which each one comprises genetic material encoding different viral proteins. This method of vaccination allows the introduction of as much as a complete set of viral genes into the individual without the risk of assembling an infectious viral particle. Thus, an immune response against most or all of the virus can be invoked in the vaccinated individual. Injection of each inoculant is performed at different sites, preferably at a distance to ensure no cells receive both genetic constructs. As a further safety precaution, some genes may be deleted or altered to further prevent the capability of infectious viral assembly.

As used herein, the term "pharmaceutical kit" is meant to collectively refer to multiple inoculant used in the present invention. Such kits include separate containers containing different inoculants and/or GVFs. It is intended that these kits be provided to include a set of inoculants used in immunizing methods and/or a therapeutic methods.

The methods of the present invention are useful in the fields of both human and veterinary medicine. Accordingly, the present invention relates to genetic immunization of mammals, birds and fish. The methods of the present invention can be particularly useful for mammalian species including human, bovine, ovine, porcine, equine, canine and feline species.

The Examples set out below include representative examples of aspects of the present invention. The Examples are not meant to limit the scope of the invention but rather serve exemplary purposes. In addition, various aspects of the invention can be summarized by the following description. However, this description is not meant to limit the scope of the invention but rather to highlight various aspects of the invention. One having ordinary skill in the art can readily appreciate additional aspects and embodiments of the invention.

EXAMPLES

Example 1

The present invention provides an HIV vaccine using direct genetic immunization. Genetic constructs are provided which, when delivered into the cells of an individual, are expressed to produce HIV proteins. According to some embodiments, the production of all viral structural proteins in the cells of the individual elicit a protective immune response which protects against HIV infection. The HIV vaccine of the present invention may be used to immunize uninfected individuals from HIV infection or serve as an immunotherapeutic for those individuals already infected. The HIV vaccine of the present invention invokes an immune response including CTLs which recognize and attack HIV infected cells and recognize the widest contingent of HIV protein. Thus, uninfected individuals are protected from HIV infection.

In some embodiments, the present invention relates to a method of immunizing an individual against HIV by administering two inoculants. These two inoculants comprise at least two and preferably more than two, a plurality or all of the genes of the HIV virus. However, the inoculants are not delivered together. Accordingly, an inoculated cell will not be administered a complete complement of genes. The vaccinated individual will receive at least two different and preferably more than two, more preferably a plurality or all of the viral genes. Immune responses can then be directed at the total complement of HIV protein target.

This strategy increases the probability that genetic material encoding the most effective target protein will be included in the vaccine and reduces the likelihood that a viral particle will escape detection by the immune response despite structural changes in one or more viral proteins which occur when the virus undergoes mutation. Accordingly, it is desirable to vaccinate an individual with multiple and preferably a nearly complete or complete complement of genes encoding viral proteins.

If a single cell is provided with a complete complement of viral genes, it is possible that a complete infectious virus can be assembled within the cell. Accordingly, a genetic construct according to the present invention is not provided with such a full complement of genes. Furthermore, two or more inoculants, each having an incomplete set of genes and combined having up to a full complement of viral genes, are administered to different cells, preferably at a distant site from each other to ensure that no vaccinated cell will inadvertently be exposed to a full set of genes. For example, a portion of the HIV genome may be inserted into a first construct and the remaining portion of the HIV genome is inserted in a second construct. The first construct is administered to an individual as a genetic vaccine in the muscle tissue of one arm while the second construct is administered to an individual as a genetic vaccine in the muscle tissue of the individual's other arm. The individual may be exposed to a full set of viral genes; thus essentially vaccinating against the whole virus but with no risk that an infectious viral particle will be assembled.

As an additional safety precaution, even when genetic material is delivered by two or more inoculants at distant parts of the individual's body, one or more essential genes can be deleted or intentionally altered to further ensure that an infectious viral particle cannot be formed. In such embodiments, the individual is not administered a complete functional set of viral genes.

A further safety precaution provides non-overlapping portions of the viral genome on the separate genetic constructs that make up the separate inoculants respectively. Accordingly, recombination between the two genetic constructs is prevented.

In some embodiments of the present invention, a full complement of structural genes are provided. The structural genes of HIV consist of gag, pol and env. These three genes are provided on two different DNA or RNA constructs. Accordingly, in one preferred embodiment, gag and pol are on one DNA or RNA construct and env is on another. In another preferred embodiment, gag is on one DNA or RNA construct and pol and env is on the other. In another preferred embodiment, gag and env are on one DNA or RNA construct and pol is on the other. In some preferred embodiments, constructs that contain rev have a splice acceptor upstream of the start codon for rev. In some preferred embodiments, constructs that contain gag have a splice donor upstream of the gag translational start codon. Optionally, in any of these combinations, HIV regulatory genes may also be present. The HIV regulatory genes are: vpr, vif, vpu, nef, tat and rev.

The DNA construct in a preferred embodiment consists of a promoter, an enhancer and a polyadenylation signal. The promoter may be selected from the group consisting of: HIV LTR, human Actin, human Myosin, CMV, RSV, Moloney, MMTV, human Hemoglobin, human muscle creatine and EBV. The enhancer may be selected from the group consisting of: human Actin, human Myosin, CMV, RSV, human Hemoglobin, human muscle creatine and EBV. The polyadenylation signal may be selected from the group consisting of: LTR polyadenylation signal and SV40 polyadenylation signal, particularly the SV40 minor polyadenylation signal among others.

In some embodiments, the two inoculant vaccine is administered intramuscularly at spatially segregated tissue of the individual, preferably in different appendages, such as for example in the right and left arms. Each inoculant of the present invention may contain from about 0.1 to about 1000 micrograms of DNA. Preferably, each inoculant contains about 1 to about 500 micrograms of DNA. More preferably, each inoculant contains about 25 to about 250 micrograms of DNA. Most preferably, each inoculant contains about 100 micrograms DNA.

The inoculant in some embodiments is in a sterile isotonic carrier, preferably phosphate buffered saline or saline solution.

In some embodiments, prior to vaccine administration, the tissue to be vaccinated is injected with a genetic vaccine facilitator, as described and discussed above. Injections of GVFs may be performed up to about 24 hours prior to vaccination. It is contemplated that GVFs will be administered immediately before or simultaneously with administration of the gene construct. The GVF is administered to the site where the gene construct is to be administered. It is also contemplated that the GVF can be administered after administration of the genetic constructs, such as immediately afterward.

In other embodiments, a genetic vaccine facilitator, as described and discussed above, is administered together with the genetic construct as a single pharmaceutical composition. The GVF and genetic construct may be combined immediately before administration of the mixture. In some preferred embodiments, a genetic vaccine facilitator, as described and discussed above, is formulated together with the genetic construct as a single pharmaceutical composition.

Accordingly, some embodiments comprise a two inoculant vaccine: one inoculant comprising a DNA or RNA construct having two HIV structural genes, the other inoculant comprising a DNA or RNA construct having the third, remaining HIV structural gene such that the combined inoculants contain a full complement of HIV structural genes. The structural genes on each DNA construct are operably linked to a promoter, an enhancer and a polyadenylation signal. The same or different regulatory elements may control expression of the viral genes. When vaccinating an individual, the two inoculants are administered intramuscularly to different sites, preferably on different arms.

In some embodiments of the invention, a genetic vaccine facilitator as discussed and described above is administered at the site where inoculant is to be administered.

In some embodiments of the invention, the genetic vaccine facilitator is included in the formulations together with the genetic constructs.

In some embodiments, the vaccination procedure is repeated at least once and preferably two or three times. Each vaccination procedure is performed from 24 hours to two months apart.

In some embodiments, the vaccine is administered using a needleless injection device. In some embodiments, the vaccine is administered hypodermically using a needleless injection device thus providing intramuscular, intradermal, subcutaneous administration simultaneously while also administering the material interstitially.

Preferred genetic constructs include the following.
Plasmids and Cloning Strategies:

Two plasmids were constructed: one which contains HIV gag/pol and the other which contains HIV env.

The HIV-1 genomic clone pNL43 was obtained through the NIH AIDS Research and Reference Reagent Program (ARRRP), Division of AIDS, NIAID, NIH, from Dr. Malcolm Martin, and can be used as the starting material for HIV-1 viral genes for genetic constructs. Alternatively, any HIV molecular clone of infected cell can, through use of the polymerase chain technology, be modified sufficiently for construction including the HXB2 clone the MN clone as well as the SF or BAL-1 clone. The pNL43 clone is a construct that consists of HIV-1 proviral DNA plus 3 kb of host sequence from the site of integration cloned into pUC18.

Construction of pNL-puro-env⁻ Plasmid:

This plasmid was constructed for expression of gag pol. The StuI site within the non-HIV 5' flanking human DNA of pNL43 was destroyed by partial digestion with StuI followed by digestion of the free ends with E. coli polymerase 1. The linear plasmid was filled and then self ligated, leaving a unique StuI site within the HIV genome. This plasmid, pNLDstu, was then digested with the blunting enzymes StuI and BsaBI which eliminated a large section of the coding sequence for gp120. The SV40 promoter and puromycin resistance coding region (puromycin acetyl transferase (PAC)) were isolated from pBABE-puro (Morgenstern and Land, 1990 Nucl. Acids Res. 18(12):3587–3596, which is incorporated herein by reference, kindly provided by Dr. Hartmut Land of the Imperial Cancer Research Fund) using EcoRI and ClaI. This fragment was blunted, then cloned into the StuI/BsaBI-digested pNLDstu. A clone was selected with the SV40-puro fragment in the correct orientation so that the 3' LTR of HIV could provide poly A functions for the PAC message. This plasmid was designated pNLpuro.

Cloning Strategy for Deletion of Vpr Regulatory Gene From the HIV gag pol V–ector:

A region from just upstream of the unique PflMI site to just after the vif termination codon was amplified via PCR using primers that introduced a non-conservative amino acid change (glu→val) at amino acid 22 of vpr, a stop codon in the vpr reading frame immediately after amino acid 22, and an EcoRI site immediately following the new stop codon. This PCR fragment was substituted for the PflMI-EcoR I fragment of NLpuro or pNL43. This substitution resulted in the deletion of 122 nucleotides of the open reading frame of vpr, thus eliminating the possibility of reversion that a point mutation strategy entails. The resulting plasmids, pNLpuroΔvpr, encode the first 21 natural amino acids of vpr plus a valine plus all other remaining HIV-1 genes and splice junctions in their native form. Such deletion strategy would also be applicable to nef, vif, and vpu and allow for structural gene expression but protect from the generation of a live recombinant virus.

Plasmid Construction for Envelope Expression:

The DNA segment encoding the envelope gene of HIV-1 HXB2 was cloned by the polymerase chain reaction (PCR) amplification technique utilizing the lambda cloned DNA obtained from the AIDS Research and Reference Reagent Program. The sequences of the 5' and 3' primers are 5'-AGGCGTCTCGAGACAGAGGAGAGCAAGAAATG-3' (SEQ ID NO:1) with incorporation of XhoI site and 5'-TTTCCCTCTAGATAAGCCATCCAATCACAC-3' (SEQ ID NO: 2) with incorporation of XbaI site, respectively, which encompass gp160, tat and rev coding region. Gene specific amplification was performed using Taq DNA polymerase according to the manufacturer's instructions (Perkin-Elmer Cetus Corp.). The PCR reaction products were treated with 0.5 µg/ml proteinase K at 37° C. for thirty minutes followed by a phenol/chloroform extraction and ethanol precipitation. Recovered DNA was then digested with XhoI and XbaI for two hours at 37° C. and subjected to agarose gel electrophoresis. The isolated and purified XhoI-XbaI PCR fragment was cloned into Bluescript plasmid (Stratagene Inc., La Jolla, Calif.) and then subcloned into the eukaryotic expression vector pMAM-neoBlue (Clontech Laboratories, Inc., Palo Alto, Calif.). The resulting construct was designated as pM160 (FIG. 1). The plasmid DNA was purified with CsCl gradient ultracentrifugation. The DNA construct pM160 encodes the HIV-1/HXB2 (Fisher, A. G., et al., (1985) Nature 316:262–265) gp160 membrane bound glycoprotein under control of a RSV enhancer element with the MMTV LTR as a promoter.

An Alternative Envelope Expression Plasmid Construction Called HIV-1 Env-rev Plasmid:

The region encoding the two exons of rev and the vpu and envelope open reading frames of HIV-1 HXB2 was amplified via PCR and cloned into the expression vector pCNDA/neo (Invitrogen). This plasmid drives envelope production through the CMV promoter.

Production and Purification:

The plasmid in *E. coli* (DH5 alpha) is grown up as follows: An LB plus ampicillin agar plate is streaked with the desired plasmid culture from frozen stock. The plate is incubated overnight (14–15 hours) at 37° C. A single colony is taken from the plate and inoculated into 15 ml of LB medium with a peptone preparation and 50 $\mu$g/ml ampicillin. This culture is grown at 37° C. while being shaken (ca. 175 rpm) for 8–10 hours. $OD_{600}$ readings should be at least 1.0. 1 liter of LB medium with peptone and 50 $\mu$g/ml ampicillin is inoculated with 1.0 OD of culture. These 1–2 liter cultures are grown overnight at 37° C. while being shaken (175 rpm).

Plasmid grown in *E. coli* (strain DH5 alpha) are harvested and purified by the following methods. General procedures for the lysis of cells and purification of plasmid can be found in "Molecular Cloning: A Laboratory Manual", 2nd Edition, J. Sambrook, E. F. Fritsch, and T. Maniatis, Cold Spring Harbor Press, 1989. The cells are concentrated and washed with glucose-tris-EDTA pH 8.0 buffer. The concentrated cells are lysed by treatment with lysozyme and briefly treated with 0.2 N KOH, the pH is then adjusted 5.5 with potassium acetate/acetic acid buffer. Insoluble material is removed by centrifugation. To the supernatant is added 2-propanol to precipitate the plasmid. The plasmid is redissolved in tris-EDTA buffer and further purified by phenol/chloroform extraction and an additional precipitation with 2-propanol.

Endotoxin can optionally be removed by a variety of methods including the following: specific adsorption by immobilized materials such as polymyxin (Tani et al., *Biomater. Artif. Cells Immobilization Biotechnol.* 20(2–4): 457–62 (1992); Issekutz, *J. Immunol. Methods* 61(3): 275–81 (1983)); anti-endotoxin monoclonal antibodies, such as 8A1 and HA-1A™ (Centocor, Malvern, Pa.; Bogard et al. *J. Immunol.* 150(10):4438–4449 (1993); Rietschel et al., *Infect. Immunity* page 3863 (1993)); positively charged depth filters (Hou et al., *J. Parenter. Sci. Technol.* 44(4): 204–9 (July–August 1990)); poly(gamma-methyl L-glutamate), Hirayama et al., *Chem. Pharm. Bull.* (Tokyo) 40(8):2106–9 (1992)); histidine (Matsumae et al., *Biotechnol. Appl. Biochem.* 12:(2):129–40 (1990)); hydrophobic interaction columns and membranes (Aida et al., *J. Immunol Methods* 132(2):191–5 (1990); Umeda et al., *Biomater Artif Cells Artif Organs* 18(4):491–7 (1990); Hou et al., *Biochem. Biophys. Acta* 1073(1):149–54 (1991); Sawada et al., *J. Hyg.* (London) 97(1):103–14 (1986)); specific hydrophobic resins useful for removing endotoxin including hydrophobic polystyrene/divinylbenzene or divinylbenzene resins such as Brownlee Polypore Resin (Applied Biosystems, Palo Alto, Calif.); XUS 40323.00 (Dow Chemical, Midland, Mich.); HP20, CHP20P (Mitsubishi Kasei, U.S.); Hamilton PRP-1, PRP-infinity (Hamilton, Reno, Nev.); Jordi Reversed-Phase DVB, Jordi Gel DVB, Polymer Labs PLgel™ (Alltech, Deerfield, Ill.); Vydac PLx™ (Separations Group, Hesperia, Calif.); other endotoxin removing materials and methods include Detoxi-Gel™ Endotoxin Removing Gel (Pierce Chemical, Rockford, Ill.); Application Note 206, (Pharmacia Biotech Inc, Piscataway, N.J.). See also generally, Sharma, *Biotech. App. Biochem.* 8:5–22 (1986). Preferred anti-endotoxin monoclonal antibodies bind to the conserved domains of endotoxin, preferably antibodies to lipid A, the most structurally conserved portion of the endotoxin molecule. Such anti-lipid A monoclonal antibodies include the high affinity murine IgG monoclonal antibody 8A1 and the human anti-lipid A IgM(k) monoclonal antibody HA-1A™. HA-1A™ was derived from a human B *E. coli* J5 vaccine. HA-1A™. HA-1A™ is reported to be broadly cross-reactive with a variety of bacterial endotoxins (lipopolysaccharides).

Example 2

The following is a list of constructs which may be used in the methods of the present invention. The vector pBabe.puro, which is used as a starting material to produce many of the below listed constructs, was originally constructed and reported by Morgenstern, J. P. and H. Land, 1990 *Nucl. Acids Res.* 18(12):3587–3596, which is incorporated herein by reference. The pBabe.puro plasmid is particularly useful for expression of exogenous genes in mammalian cells. DNA sequences to be expressed are inserted at cloning sites under the control of the Moloney murine leukemia virus (Mo MuLV) long terminal repeat (LTR) promoter. The plasmid contains the selectable marker for puromycin resistance.

Example 3

Plasmid pBa.V$\alpha$3 is a 7.8 kb plasmid that contains a 2.7 kb EcoRI genomic fragment encoding the T cell receptor V$\alpha$3 region containing the L, V and J segments cloned into the EcoRI site of pBabe.puro. The T cell receptor-derived target protein is useful in the immunization against and treatment of T cell mediated autoimmune disease and clonotypic T cell lymphoma and leukemia.

Example 4

Plasmid pBa.gagpol-vpr is a 9.88 kb plasmid that contains the gag/pol and vif genes from HIV/MN cloned into pBabe.puro. The vpr gene is deleted. The plasmid which contains these HIV viral genes, which encode HIV target proteins, is useful in the immunization against and treatment of HIV infection and AIDS. The HIV DNA sequence is published in Reiz, M. S., 1992 *AIDS Res. Human Retro.* 8:1549, which is incorporated herein by reference. The sequence is accessible from Genbank No.: M17449, which is incorporated herein by reference.

Example 5

Plasmid pM160 is an 11.0 kb plasmid that contains the 2.3 kb PCR fragment encoding the HIV-I/3B envelope protein and rev/tat genes cloned into pMAMneoBlue. The nef region is deleted. The plasmid which contains these HIV viral genes, which encode HIV target proteins, is useful in the immunization against and treatment of HIV infection and AIDS. The DNA sequence of HIV-1/3B is published in Fisher, A., 1985 *Nature* 316:26672, which is incorporated herein by reference. The sequence is accessible from Genbank No.: K03455, which is incorporated herein by reference.

Example 6

Plasmid pBa.VL is a 5.4 kb plasmid that contains PCR fragment encoding the VL region of an anti-DNA antibody cloned into pBabe.puro at the XbaI and EcoRI sites. The antibody-derived target protein is an example of a target protein useful in the immunization against and treatment of B cell mediated autoimmune disease and clonotypic B cell lymphoma and leukemia. A general method for cloning functional variable regions from antibodies can be found in Chaudhary, V. K., et al., 1990 *Proc. Natl. Acad. Sci. USA* 87:1066, which is incorporated herein by reference.

Example 7

Plasmid pOspA.B is a 6.84 kb plasmid which contains the coding regions encoding the OspA and OspB antigens of the *Borrelia burgdorferi*, the spirochete responsible for Lyme's disease cloned into pBabe.puro at the BamHI and SalI sites. The PCR primers used to generate the OspA and OspB fragments are 5'-GAAGGATCCATGAAAAAATATTTATTGGG-3' (SEQ ID NO:3) and 5'-ACTGTCGACTTATTTTAAAGCGTTTTTAAG-3' (SEQ ID NO: 4). See: Williams, W. V., et al. 1992 *DNA and Cell. Biol.* 11(3):207, which is incorporated herein by reference. The plasmid which contains these pathogen genes, which encode target proteins, is useful in the immunization against Lyme's disease.

Example 8

Plasmid pBa.Rb-G is a 7.10 kb plasmid which contains a PCR generated fragment encoding the rabies G protein cloned into pBabe.puro at the BamHI site. The plasmid which contains this pathogen gene, which encodes the rabies G protein, is useful in the immunization against Rabies. The DNA sequence is disclosed in Genebank No.:M32751, which is incorporated herein by reference. See also: Anilionis, A., et al., 1981 *Nature* 294:275, which is incorporated herein by reference.

Example 9

Plasmid pBa.HPV-L1 is a 6.80 kb plasmid which contains a PCR generated fragment encoding the L1 capsid protein of the human papillomavirus (HPV) including HPV strains 16, 18, 31 and 33 cloned into pBabe.puro at the BamHI and EcoRI sites. The plasmid is useful in the immunization against HPV infection and the cancer caused thereby. The DNA sequence is disclosed in Genebank No.:M15781, which is incorporated herein by reference. See also: Howley, P., 1990 *Fields Virology*, Volume 2, Eds.: Channock, R. M. et al. Chapter 58:1625; and Shah, K. and P. Howley, 1990 *Fields Virology*, Volume 2, Eds.: Channock, R. M. et al. Chapter 59; both of which are incorporated herein by reference.

Example 10

Plasmid pBa.HPV-L2 is a 6.80 kb plasmid which contains a PCR generated fragment encoding the L2 capsid protein of the human papillomavirus (HPV) including HPV strains 16, 18, 31 and 33 cloned into pBabe.puro at the BamHI and EcoRI sites. The plasmid is useful in the immunization against HPV infection and the cancer caused thereby. The DNA sequence is disclosed in Genebank No.:M15781, which is incorporated herein by reference. See also: Howley, P., 1990 *Fields Virology*, Volume 2, Eds.: Channock, R. M. et al. Chapter 58:1625; and Shah, K. and P. Howley, 1990 *Fields Virology*, Volume 2, Eds.: Channock, R. M. et al. Chapter 59; both of which are incorporated herein by reference.

Example 11

Plasmid pBa.MNp7 is a 5.24 kb plasmid which contains a PCR generated fragment encoding the p7 coding region including the HIV MN gag (core protein) sequence cloned into pBabe.puro at the BamHI site. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.:M17449, which is incorporated herein by reference.

Example 12

Plasmid pGA733-2 is a 6.3 kb plasmid that contains the GA733-2 tumor surface antigen cloned from the colorectal carcinoma cell line SW948 into pCDM8 vector (Seed, B. and A. Aruffo, 1987 *Proc. Natl. Acad. Sci. USA* 84:3365, which is incorporated herein by reference) at BstXI site. The tumor-associated target protein is an example of a target protein useful in the immunization against and treatment of hyperproliferative disease such as cancer. The GA733-2 antigen is a useful target antigen against colon cancer. The GA733 antigen is reported in Szala, S. et al., 1990 *Proc. Natl. Acad. Sci. USA* 87:3542–3546, which is incorporated herein by reference.

Example 13

Plasmid pT4-pMV7 is a 11.15 kb plasmid that contains cDNA which encodes human CD4 receptor cloned into pMV7 vector at the EcoRI site. The CD4 target protein is useful in the immunization against and treatment of T cell lymphoma. Plasmid pT4-pMV7 is available from the AIDS Repository, Catalog No. 158.

Example 14

Plasmid pDJGA733 is a 5.1 kb plasmid that contains the GA733 tumor surface antigen cloned into pBabe.puro at the BamHI site. The tumor-associated target protein is an example of a target protein useful in the immunization against and treatment of hyperproliferative disease such as cancer. The GA733 antigen is a useful target antigen against colon cancer.

Example 15

Plasmid pBa.RAS is a 6.8 kb plasmid that contains the ras coding region that was first subcloned from pZIPneoRAS and cloned into pBabe.puro at the BamHI site. The ras target protein is an example of a cytoplasmic signalling molecule. The method of cloning ras is reported in Weinberg 1984 *Mol. Cell. Biol.* 4:1577, which is incorporated herein by reference. Ras encoding plasmid are useful for the immunization against and treatment of hyperproliferative disease such as cancer; in particular, ras related cancer such as bladder, muscle, lung, brain and bone cancer.

Example 16

Plasmid pBa.MNp55 is a 6.38 kb plasmid which contains a PCR generated fragment encoding the p55 coding region including the HIV MN gag precursor (core protein) sequence cloned into pBabe.puro at the BamHI site. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.:M17449, which is incorporated herein by reference.

Example 17

Plasmid pBa.MNp24 is a 5.78 kb plasmid which contains a PCR generated fragment from the pMN-SF1 template encoding the p24 coding region including the whole HIV MN gag coding region cloned into pBabe.puro at the BamHI and EcoRI sites. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.: M17449, which is incorporated herein by reference.

Example 18

Plasmid pBa.MNp17 is a 5.5 kb plasmid which contains a PCR generated fragment encoding the p17 coding region including the HIV MN gag (core protein) sequence cloned into pBabe.puro at the BamHI and EcoRI sites. The plasmid which contains these HIV viral genes, which encode HIV target proteins, is useful in the immunization against and treatment of HIV infection and AIDS. Reiz, M. S., 1912092 *AIDS Res. Human Retro.* 8:1549, which is incorporated herein by reference. The sequence is accessible from Genbank No.: M17449, which is incorporated herein by reference.

Example 19

Plasmid pBa.SIVenv is a 7.8 kb plasmid which contains a 2.71 PCR generated fragment amplified from a construct containing SIV 239 in pBR322 cloned into pBabe.puro at the BamHI and EcoRI sites. The primers used are 5'-GCCAGTTTTGGATCCTTAAAAAGGCTTGG-3' (SEQ ID NO:5) and 5'-TTGTGAGGGACAGAATTCCAATCAGGG-3' (SEQ ID NO:6). The plasmid is available from the AIDS Research and Reference Reagent Program; Catalog No. 210.

Example 20

Plasmid pcTSP/ATK.env is a 8.92 kb plasmid which contains a PCR generated fragment encoding the complete HTLV envelope coding region from HTLV-1/TSP and /ATK isolates subcloned into the pcDNA1/neo vector. The primers used are 5'-CAGTGATATCCCGGGAGACTCCTC-3' (SEQ ID NO:7) and 5'-GAATAGAAGAACTCCTCTAGAATTC-3' (SEQ ID NO:8). Plasmid pcTSP/ATK.env is reported in 1988 *Proc. Natl. Acad. Sci. USA* 85:3599, which is incorporated herein by reference. The HTLV env target protein is useful in the immunization against and treatment of infection by HTLV and T cell lymphoma.

Example 21

Plasmid pBa.MNgp160 is a 7.9 kb plasmid which contains a 2.8 kb PCR generated fragment amplified from a construct containing MNenv in pSP72 and cloned into pBabe.puro at the BamHI and EcoRI sites. The primers used are 5'-GCCTTAGGCGGATCCTATGGCAGGAAG-3' (SEQ ID NO:9) and 5'-TAAGATGGGTGGCCATGGTGAATT-3' (SEQ ID NO:10). Reiz, M. S., 1992 *AIDS Res. Human Retro.* 8:1549, which is incorporated herein by reference. The sequence is accessible from Genbank No.:M17449, which is incorporated herein by reference. The plasmid which contains these HIV viral genes, which encode HIV target proteins, is useful in the immunization against and treatment of HIV infection and AIDS.

Example 22

Plasmid pC.MNp55 is a 11.8 kb plasmid which contains a 1.4 kb PCR generated fragment amplified from the gag region of MN isolate and cloned into the pCEP4 vector. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.: M17449, which is incorporated herein by reference.

Example 23

Plasmid pC.Neu is a 14.2 kb plasmid that contains a 3.8 kb DNA fragment containing the human neu oncogene coding region that was cut out from the LTR-2/erbB-2 construct and subcloned into the pCEP4 vector. The pC.Neu plasmid is reported in DiFiore 1987 *Science* 237:178, which is incorporated herein by reference. The neu oncogene target protein is an example of a growth factor receptor useful as a target protein for the immunization against and treatment of hyperproliferative disease such as cancer; in particular, colon, breast, lung and brain cancer.

Example 24

Plasmid pC.RAS is a 11.7 kb plasmid that contains a 1.4 kb DNA fragment containing the ras oncogene coding region that was first subcloned from pZIPneoRAS and subcloned into pCEP4 at the BamHI site. The pC.RAS plasmid is reported in Weinberg 1984 *Mol. Cell. Biol.* 4:1577, which is incorporated herein by reference. The ras target protein is an example of a cytoplasmic signalling molecule. Ras encoding plasmid are useful for the immunization against and treatment of hyperproliferative disease such as cancer; in particular, ras related cancer such as bladder, muscle, lung, brain and bone cancer.

Example 25

Plasmid pNLpuro is a 15 kb plasmid which contains HIV gag/pol and SV40-puro insertion. The plasmid which contains these HIV viral genes which encode HIV target proteins, is useful in the immunization against and treatment of HIV infection and AIDS.

Example 26

The plasmid pM160 can be used as a starting material for several plasmids useful to express one or more genes from the env portion of HIV. Construction os pM160 is described above. The plasmid encompasses gp160, tat and rev coding region. The nef gene is absent.

The promoter controlling gp160/rev/tat gene expression is MMTV LTR. The promoter may be deleted and replaced with Actin promoter, myosin promoter, HIV LTR promoter and CMV promoter.

The gene conferring ampicillin resistance may be deleted or otherwise inactivated. The gene conferring neomycin resistance may be placed under the control of a bacterial promoter.

The Rous sarcoma virus enhancer may be deleted from the plasmid. The RSV enhancer may be replaced with the muscle creatine enhancer.

The gp160/rev/tat genes overlap and share the same nucleotide sequences in different reading frames. The rev gene may be deleted by changing its initiation codon to a different codon. Similarly, the tat gene may be eliminated by the same means. In each plasmid except those using the HIV LTR promoter to control gp160/rev/tat, either rev, tat, or both rev and tat may be eliminated. In plasmids using the HIV LTR promoter, tat must be present.

The following Table lists pM160-modified plasmids. Each plasmid has an inactivated ampicillin gene. Each has deleted the RSV enhancer. Some have no enhancer (no); some have creatine muscle enhancer (CME). Some have the HIV rev gene (yes) while it is deleted in others (no). Some have the HIV tat gene (yes) while it is deleted in others (no).

| Construct | Promoter | enhancer | rev | tat |
|---|---|---|---|---|
| RA-1 | Actin | no | yes | yes |
| RA-2 | Actin | no | yes | no |
| RA-3 | Actin | no | no | yes |
| RA-4 | Actin | CME | yes | yes |
| RA-5 | Actin | CME | yes | no |
| RA-6 | Actin | CME | no | yes |
| RA-7 | CMV | no | yes | yes |
| RA-8 | CMV | no | yes | no |
| RA-9 | CMV | no | no | yes |
| RA-10 | CMV | CME | yes | yes |
| RA-11 | CMV | CME | yes | no |
| RA-12 | CMV | CME | no | yes |
| RA-13 | MMTV | no | yes | yes |
| RA-14 | MMTV | no | yes | no |
| RA-15 | MMTV | no | no | yes |
| RA-16 | MMTV | CME | yes | yes |
| RA-17 | MMTV | CME | yes | no |
| RA-18 | MMTV | CME | no | yes |
| RA-19 | Myosin | no | yes | yes |
| RA-20 | Myosin | no | yes | no |
| RA-21 | Myosin | no | no | yes |
| RA-22 | Myosin | CME | yes | yes |
| RA-23 | Myosin | CME | yes | no |
| RA-24 | Myosin | CME | no | yes |
| RA-25 | HIV-1 LTR | no | yes | yes |
| RA-26 | HIV-1 LTR | no | no | yes |
| RA-27 | HIV-1 LTR | CME | yes | yes |
| RA-28 | HIV-1 LTR | CME | no | yes |

Constructions RA-29 to RA-56 are identical to RA-1 to RA-32 respectively except in each case the promoter controlling the neomycin gene is a bacterial promoter.

Example 27

The plasmid pNLpuro may be used as a starting material to produce several different plasmids which express the HIV gag/pol genes. As described above, pNLpuro was constructed for expression of gag pol. The plasmid pNLpuroΔvpr, which is described above, was designed to delete the vpr regulatory gene from the HIV gag pol vector in order to eliminate a necessary regulatory protein from the set of genes to be introduced by vaccination. In addition to vpr, other changes may be made by those having ordinary skill in the art to plasmid pNL43puro using standard molecular biology techniques and widely available starting material.

The human flanking sequences 5' and 3' of the HIV sequences can be removed by several methods. For example, using PCR, only HIV, SV40-puro, and pUC18 sequences can be amplified and reconstructed.

The psi region of HIV, which is important in the packaging of the virus, can be deleted from pNL43puro-based plasmids. In order to delete the psi region, the pNLpuro plasmid is cut with SacI and SpeI. This digestion removes the psi region as well as the 5' LTR which is upstream and portion of the gag/pol region which is downstream of psi. In order to reinsert the deleted non-psi sequences, PCR amplification is performed to regenerate those sequences. Primers are designed which regenerate the portions of the HIV sequence 5' and 3' to psi without regenerating psi. The primers reform the SacI site at the portion of the plasmid 5' of the 5' LTR. Primers go downstream from a site upstream of the SacI site to a site just 3' of the 5' end of the psi region, generating an AatI site at the 3' end. Primers starting just 5' of the psi region also generate an AatI site and, starting 3' of the SpeI site, regenerate that site. The PCR generated fragments are digested with SacI, AatI and SpeI and ligated together with the SacI/SpeI digested pNLpuro-psi fragment. The HIV 5'LTR promoter can be deleted and replaced with Moloney virus promoter, MMTV LTR, Actin promoter, myosin promoter and CMV promoter.

The HIV 3'LTR polyadenylation site can be deleted and replaced with SV40 polyadenylation site.

The gene conferring ampicillin resistance may be deleted or otherwise inactivated.

The following is a list of pNLpuro-based constructions in which HIV psi and vpr regions are deleted and human flanking regions 5' and 3' of the HIV sequences are deleted.

| Construct | Promoter | poly(A) | Amp$^r$ |
|---|---|---|---|
| LA-1 | Moloney | HIV 3'LTR | yes |
| LA-2 | Moloney | SV40 | yes |
| LA-3 | Moloney | HIV 3'LTR | no |
| LA-4 | Moloney | SV40 | no |
| LA-5 | CMV | HIV 3'LTR | yes |
| LA-6 | CMV | SV40 | yes |
| LA-7 | CMV | HIV 3'LTR | no |
| LA-8 | CMV | SV40 | no |
| LA-9 | MMTV | HIV 3'LTR | yes |
| LA-10 | MMTV | SV40 | yes |
| LA-11 | MMTV | HIV 3'LTR | no |
| LA-12 | MMTV | SV40 | no |
| LA-13 | HIV 5'LTR | HIV 3'LTR | yes |
| LA-14 | HIV 5'LTR | SV40 | yes |
| LA-15 | HIV 5'LTR | HIV 3'LTR | no |
| LA-16 | HIV 5'LTR | SV40 | no |

Constructions LA-17 to LA-32 are identical to LA-1 to LA-16 respectively except in each case at least one of the human flanking sequence remains.

Example 28

In another construction for expressing the env gene, that region of HIV may be inserted into the commercially available plasmid pCEP4 (Invitrogen). The pCEP4 plasmid is particularly useful since it contains the Epstein Barr virus origin of replication and nuclear antigen EBNA-1 coding region which produces high copy episomal replication without integration. pCEP4 also contains the hygromycin marker under the regulatory control of the thymidine kinase promoter and polyadenylation site. The HIV env coding region is placed under the regulatory control of the CMV promoter and SV40 polyadenylation site. The HIV env coding region was obtained as a 2.3 kb PCR fragment form HIV/3B, Genebank sequence K03455. The resulting pCEP4-based plasmid, pRA-100, is maintained extrachromosomally and produces gp160 protein.

Example 29

In another construction for expressing the env gene, that region of HIV may be inserted into the commercially available plasmid pREP4 (Invitrogen). The pREP4 plasmid is particularly useful since it contains the Epstein Barr virus origin of replication and nuclear antigen EBNA-1 coding region which produces high copy episomal replication without integration. pREP4 also contains the hygromycin marker under the regulatory control of the thymidine kinase promoter and polyadenylation site. The HIV env coding region is placed under the regulatory control of the RSV promoter and SV40 polyadenylation site. The HIV env coding region was obtained as a 2.3 kb PCR fragment form HIV/3B, Genebank sequence K03455. The resulting pCEP4-based plasmid, pRA-101, is maintained extrachromosomally and produces gp160 protein.

Example 30

In another construction for expressing the gag/pol genes, that region of HIV may be inserted into the commercially available plasmid pCEP4 (Invitrogen). The pCEP4 plasmid is particularly useful since it contains the Epstein Barr virus origin of replication and nuclear antigen EBNA-1 coding region which produces high copy episomal replication without integration. pCEP4 also contains the hygromycin marker under the regulatory control of the thymidine kinase promoter and polyadenylation site. The HIV gag/pol coding region is placed under the regulatory control of the CMV promoter and SV40 polyadenylation site. The HIV gag/pol coding region was obtained from HIV MN, Genebank sequence MI7449, and includes the vif gene. The vpr gene is not included. The resulting pCEP4-based plasmid, pLA-100, is maintained extrachromosomally and produces GAG55, reverse transcriptase, protease and integrase proteins.

Example 31

In another construction for expressing the gag/pol genes, that region of HIV may be inserted into the commercially available plasmid pREP4 (Invitrogen). The pREP4 plasmid is particularly useful since it contains the Epstein Barr virus origin of replication and nuclear antigen EBNA-1 coding region which produces high copy episomal replication without integration. pREP4 also contains the hygromycin marker under the regulatory control of the thymidine kinase promoter and polyadenylation site. The HIV gag/pol coding region is placed under the regulatory control of the CMV promoter and SV40 polyadenylation site. The HIV gag/pol coding region was obtained from HIV MN, Genebank sequence MI7449, and includes the vif gene. The vpr gene is not included. The resulting pREP4-based plasmid, pLA-101, is maintained extrachromosomally and produces GAG55, reverse transcriptase, protease and integrase proteins.

Example 32

The following construction, referred to herein as pGAGPOL.rev, is useful to express HIV gag/pol genes.

The plasmid includes a Kanamycin resistance gene and a pBR322 origin of DNA replication. The sequences provided for transcription regulation include: a cytomegalovirus promoter; a Rous sarcoma virus enhancer; and an SV40 polyadenylation signal. The HIV-1 sequences included in pGAGPOL.rev include a sequence that encodes p17, p24, and p15 of the gag open reading frame; a sequence that encodes protease, a sequence that encodes reverse transcriptase which contains a small deletion and a sequence that encodes the inactive amino terminus of integrase of the pol open reading frame; and a sequence that encodes rev. Each of the HIV sequences are derived from HIV-1 strain HXB2.

Several safety features are included in pGAGPOL.rev. These include use of the CMV promoter and a non-retroviral poly(A) site. Furthermore, deletion of the ψ sequence limits the ability to package viral RNA. In addition, multiple mutations of the reverse transcriptase yield an enzymatically inactive product. Moreover, a large deletion of integrase yields an inactive product and a Kanamycin resistance marker is used for stabilizing bacterial transformants.

Plasmid pGAGPOL.rev is constructed as follows.

Step 1. A subclone of part of the HIV-1 (HXB2) genome that is cloned into Bluescript (Stratagene) is used. The subclone of HIV-1 contains the complete 5'LTR and the rest of the HIV-1 genome to nucleotide 5795 (Genebank numbering). The HIV-1 sequences are obtained from the HXB2D plasmid (AIDS Repository).

Step 2. PCR part of gag from the open reading frame HXB2D plasmid (AIDS Repository). Cut PCR fragment with NotI and SpeI and ligate with HIV-1 subclone described above restricted with NotI and SpeI.

Step 3. PCR gag/pol junction and part of pol-encoding sequences from the HXB2D plasmid (AIDS Repository) with primers SEQ ID NO:11 and SEQ ID NO:12. Cut PCR product with ClaI and ligate together. Cut ligated fragments with BclI and SalI and ligate with plasmid from Step 2 digested with BclI and SalI.

Step 4. Cut plasmid from Step 3 with BspMI and EcoRI and religate with adapters formed by annealing linkers SEQ ID NO:13 and SEQ ID NO:14.

Step 5. Cut plasmid from Step 4 with NotI and SalI and ligate with plasmid from either 4a or 4b in description written for pENV (below). Cut also with NotI and SalI.

Step 6. Restrict plasmid from Step 5 with SalI and MluI and ligate with PCR product obtained by PCR of rev with primers SEQ ID NO:15 and SEQ ID NO:16.

Step 7. Cut plasmid from Step 6 with NotI and ligate with product obtained by PCR of the rev responsive element in the HXB2D plasmid (AIDS Repository) with primers SEQ ID NO:17 and SEQ ID NO:18.

Steps 6 and 7 are optional.

Example 33

The following construction, referred to herein as pENV, is useful to express HIV env genes.

The plasmid includes a Kanamycin resistance gene and a pBR322 origin of DNA replication. The sequences provided for transcription regulation include: a cytomegalovirus promoter; a Rous sarcoma virus enhancer; and an SV40 polyadenylation signal. The HIV-1 sequences included in pENV include a sequence that encodes vpu; a sequence that encodes rev; a sequence that encodes gp160; a sequence that encodes 50% of nef; a sequence that encodes vif; and, a sequence that encodes vpr with a 13 amino acid carboxy-end deletion. The vpu, rev, gp160 and nef sequences are derived from HIV-1 strain MN. The vif and vpr sequences are derived from HIV-1 strain HXB2.

Several safety features are included in pGAGPOL.rev. These include use of the CMV promoter and a non-retroviral poly(A) site. Furthermore, tat has been deleted and a 50% deletion of nef yields an "inactive" nef product. In addition, vif and vpr are placed out of normal sequence and a partial deletion of vpr further ensures an inactive vpr product.

Plasmid pENV is constructed as follows.

Step 1. Start with pUC18 digested with HindIII and EcoRI. The resulting fragment that contains the ColE1 origin of replication and the laci gene should be ligated with the EcoRI/HindIII fragment from pMAMneoBlue that contains the our sarcoma virus enhancer. The resulting plasmid or pMAMneo-Blue from Clontech (Palo Alto, Calif.) can then be digested with HindIII and BglI. Using standard techniques, ligate with fragment containing kan gene obtained by PCR of geneblock plasmid (Pharmacia).

Step 2. If pMAMneo-Blue used as starting plasmid, digest with MluI and EcoRI, fill in the ends with Klenow fragment of Polymerase I and religate.

Step 3. Them, with either pMAMneo-Blue or pUC18-derived plasmid, digest with HindIII and ligate with the SV40 polyA site and early splicing region obtained by PCR of pCEP4 (Invitrogen, San Diego Calif.) with primers SEQ ID NO:19 and SEQ ID NO:20.

Step 4a. Digest with BamHI and ligate with the CMV promoter obtained by PCR of pCEP4 (Invitrogen, San Diego Calif.) with primers SEQ ID NO:21 and SEQ ID NO:22.

Step 4b. Digest with BamHI and ligate with the MOMLV LTR obtained by PCR with primers SEQ ID NO:23 and SEQ ID NO:24.

Step 5. Digest with NotI and MluI and ligate with GP160 coding region obtained by PCR of pMN-ST1 with primers SEQ ID NO:25 and SEQ ID NO:26.

Step 6. Digest with MluI and ligate with sequences that encode vif in its entirety and vpr with a 13aa carboxy-end deletion by CPR of HXB2D plasmid (AIDS Repository) with primers SEQ ID NO:27 and SEQ ID NO:28.

Example 34

In some embodiments, the present invention relates to a method of immunizing an individual against HIV by administering a single inoculant. This inoculant includes a genetic construct that comprises at least one, preferably two, more preferably more than two or a plurality of the genes of the HIV virus or all of the structural genes. However, the inoculant does not contain a complete complement of all HIV genes. If a single cell is provided with a complete complement of viral genes, it is possible that a complete infectious virus can be assembled within the cell. Accordingly, a genetic construct according to the present invention is not provided with such a full complement of genes. As a safety precaution, one or more essential genes can be deleted or intentionally altered to further ensure that an infectious viral particle cannot be formed.

In some embodiments of the present invention, at least portions of one, two or all HIV structural genes are provided. The structural genes of HIV consist of gag, pol and env. Portions of at least one of these three genes are provided on a genetic construct. Accordingly, in some embodiments, at least a portion of each of gag and pol are provided on a genetic construct; in some embodiments, at least a portion of env is provided on a genetic construct; in some embodiments, at least a portion of gag is provided on a genetic construct; in some embodiments at least a portion of each of pol and env are provided on a genetic construct; in some embodiments, at least a portion of each of gag and env are provided on a genetic construct; in some embodiments at least a portion of pol is provided on a genetic construct. Optionally, the entire gene is provided. Optionally, in any of these constructs, HIV regulatory genes may also be present. The HIV regulatory genes are: vpr, vif, vpu, nef, tat and rev.

Example 35

As used herein, the term "expression unit" is meant to refer to a nucleic acid sequence which comprises a promoter operably linked to a coding sequence operably linked to a polyadenylation signal. The coding sequence may encode one or more proteins or fragments thereof. In preferred embodiments, a expression unit is within a plasmid.

As used herein, the term "HIV expression unit" is meant to refer to a nucleic acid sequence which comprises a promoter operably linked to a coding sequence operably linked to a polyadenylation signal in which the coding sequence encodes a peptide that comprises an epitope that is identical or substantially similar to an epitope found on an HIV protein. "Substantially similar epitope" is meant to refer to an epitope that has a structure which is not identical to an epitope of an HIV protein but nonetheless invokes an cellular or humoral immune response which cross reacts to an HIV protein. In preferred embodiments, the HIV expression unit comprises a coding sequence which encodes one or more HIV proteins or fragments thereof. In preferred embodiments, an HIV expression unit is within a plasmid.

In some embodiments of the present invention, a single genetic construct is provided that has a single HIV expression unit which contains DNA sequences that encode one or more HIV proteins or fragments thereof. As used herein, the term "single HIV expression unit construct" is meant to refer to a single genetic construct that contains a single HIV expression unit. In preferred embodiments, a single HIV expression unit construct is in the form of a plasmid.

In some embodiments of the present invention, a single genetic construct is provided that has more than one HIV expression units in which each contain DNA sequences that encode one or more HIV proteins or fragments thereof. As used herein, the term "multiple HIV expression unit genetic construct" is meant to refer to a single plasmid that contains more than one HIV expression units. In preferred embodiments, a multiple HIV expression unit construct is in the form of a plasmid.

In some embodiments of the present invention, a single genetic construct is provided that has two HIV expression units in which each contain DNA sequences that encode one or more HIV proteins or fragments thereof. As used herein, the term "two HIV expression unit genetic construct" is meant to refer to a single plasmid that contains two HIV expression units, i.e a multiple HIV expression unit genetic construct that contains two HIV expression unit genetic expression units. In a two HIV expression unit genetic construct, it is preferred that one HIV expression unit operates in the opposite direction of the other HIV expression unit. In preferred embodiments, a two HIV expression unit construct is in the form of a plasmid.

In some embodiments of the present invention, an HIV genetic vaccine is provided which contains a single genetic construct. The single genetic construct may be a single HIV expression unit genetic construct, a two HIV expression unit genetic construct or a multiple HIV expression unit genetic construct which contains more than two HIV expression units.

In some embodiments of the present invention, an HIV genetic vaccine is provided which contains more than one genetic construct in a single inoculant.

In some embodiments of the present invention, an HIV genetic vaccine is provided which contains more than one genetic construct in more than one inoculant. As used herein, the term "multiple inoculant" is meant to refer to a genetic vaccine which comprises more than one genetic construct, each of which is administered separately. In some embodiments of the present invention, an HIV genetic vaccine is provided which contains two genetic constructs. Each genetic construct may be, independently, a single HIV expression unit genetic construct, a two HIV expression unit genetic construct or a multiple HIV expression unit genetic construct which contains more than two HIV expression units. In some embodiments, both genetic constructs are single HIV expression unit genetic constructs. In some embodiments, both genetic constructs are two HIV expression unit genetic constructs. In some embodiments, both genetic constructs are multiple HIV expression unit genetic constructs. In some embodiments, one genetic construct is a single HIV expression unit genetic construct and the other is a two HIV expression unit genetic construct. One having ordinary skill in the art can readily recognize and appreciate the many variations depending upon the number of genetic constructs used in a genetic vaccine and the number of HIV expression units that may be present on each genetic construct.

It is preferred that the genetic constructs of the present invention do not contain certain HIV sequences, particularly, those which play a role in the HIV genome integrating into the chromosomal material of the cell into which it is introduced. It is preferred that the genetic constructs of the present invention do not contain LTRs from HIV. Similarly, it is preferred that the genetic constructs of the present invention do not contain a psi site from HIV. Further, it is preferred that the reverse transcriptase gene is deleted and the integrase gene is deleted. Deletions include deletion of only some of the codons or replacing some of the codons in order to essentially delete the gene. For example, the initiation codon may be deleted or changed or shifted out of frame to result in a nucleotide sequence that encodes an incomplete and non-functioning.

It is also preferred that the genetic constructs of the present invention do not contain a transcribable tat gene from HIV. The tat gene, which overlaps the rev gene may be completely deleted by substituting the codons that encode rev with other codons that encode the same amino acid for rev but which does not encode the required tat amino acid in the reading frame in which tat is encoded. Alternatively, only some of the codons are switched to either change, i.e. essentially delete, the initiation codon for tat and/or change, i.e. essentially delete, sufficient codons to result in a nucleotide sequence that encodes an incomplete and non-functioning tat.

It is preferred that a genetic construct comprises coding sequences that encode peptides which have at least an epitope identical to or substantially similar to an epitope from HIV gag, pol, env or rev proteins. It is more preferred that a genetic construct comprises coding sequences that encode at least one of HIV gag, pol, env or rev proteins or fragments thereof. It is preferred that a genetic construct comprises coding sequences that encode peptides which have more than one epitopes identical to or substantially similar to an epitope from HIV gag, pol, env or rev proteins. It is more preferred that a genetic construct comprises coding sequences that encode more than one of HIV gag, pol, env or rev proteins or fragments thereof.

In some embodiments, a genetic construct comprises coding sequences that encode peptides which have at least an epitope identical to or substantially similar to an epitope from HIV vif, vpr, vpu or nef proteins. In some embodiments, a genetic construct comprises coding sequences that encode at least one of HIV vif, vpr, vpu or nef proteins or fragments thereof.

A single HIV expression unit genetic construct may comprise coding regions for one or more peptides which share at least one epitope with an HIV protein or fragment thereof in a single expression unit under the regulatory control of single promoter and polyadenylation signal. It is preferred that genetic constructs encode more than one HIV protein or fragment thereof. The promoter may be any promoter functional in a human cell. It is preferred that the promoter is an SV40 promoter or a CMV promoter, preferably a CMV immediate early promoter. The polyadenylation signal may be any polyadenylation signal functional in a human cell. It is preferred that the polyadenylation signal is an SV40 polyadenylation signal, preferably the SV40 minor polyadenylation signal. If more than one coding region is provided in a single expression unit, they may be immediately adjacent to each other or separated by non-coding regions. In order to be properly expressed, a coding region must have an initiation codon and a termination codon.

A two HIV expression unit genetic construct may comprise coding regions for one or more peptides which share at least one epitope with an HIV protein or fragment thereof on each of the two expression units. Each expression unit is under the regulatory control of single promoter and polyadenylation signal. In some embodiments, it is preferred that genetic constructs encode more than one HIV protein or fragment thereof. In some embodiments, it is preferred that nucleotide sequences encoding gag and pol are present on one expression unit and nucleotide sequences encoding env and rev are present on the other. The promoter may be any promoter functional in a human cell. It is preferred that the promoter is an SV40 promoter or a CMV promoter, preferably a immediate early CMV promoter. The polyadenylation signal may be any polyadenylation signal functional in a human cell. It is preferred that the polyadenylation signal is an SV40 polyadenylation signal, preferably the SV40 minor polyadenylation signal. If more than one coding region is provided in a expression unit, they may be immediately adjacent to each other or separated by non-coding regions. In order to be properly expressed, a coding region must have an initiation codon and a termination codon.

According to some embodiments of the present invention, the MHC Class II crossreactive epitope in env is deleted and replaced with the analogous region from HIV II.

When a genetic construct contains gag and/or pol, it is generally important that rev is also present. In addition to rev, a rev response element may be provided with gag and pol for increased expression of those genes.

When genetic constructs are produced that it is preferred that the env gene used in plasmid 1 is derived from MN or MN-like isolates including clinical isolates resembling MN, preferably non-syncytial inducing clinical isolates, preferably those that are macrophage tropic from early stage clinical isolates.

Multiple proteins may be produced from a single expression unit by alternative splicing. Splicing signals are provided to allow alternative splicing which produces different messages encoding different proteins.

Example 36

FIG. 4 shows four backbones, A, B, C and D. FIG. 5 shows 4 inserts, 1, 2, 3 and 4. Insert 1 supports expression of gag and pol; the rev response element was cloned in a manner to conserve the HIV splice acceptor. Insert 2 is similar to insert 1 as it too supports expression of gag and pol except the rev response element was cloned without conserving the HIV splice acceptor. Insert 3 supports expression of gag and pol, includes a deletion of the integrase gene and does not include the presence of the cis acting rev response element. Insert 4 supports expression of rev, vpu and env. The env may have the MHC class II cross reactive epitope altered to eliminate crossreactivity and the V3 loop may be altered to eliminate the possibility of syncytia formation.

In some embodiments, backbone A is used with insert 1. Such constructs optionally contain the SV40 origin of replication. Plasmid pA1ori+ is backbone A with insert 1 and the SV40 origin of replication. Plasmid pA1ori− is backbone A with insert 1 without the SV40 origin of replication. Additionally, either pA1ori+ or pA1ori− may include integrase yielding pA1ori+int+ and pA1ori−int+, respectively. Plasmids pA1ori+, pA1ori−, pA1ori+int+ and pA1ori−int+ may be further modified by functionally deleing the reverse transcriptase (RT) gene yielding pA1ori+RT−, pA1ori−RT−, pA1ori+int+RT− and pA1ori−int+RT−, respectively.

In some embodiments, backbone A is used with insert 2. Such constructs optionally the SV40 origin of replication. Plasmid pA2ori+ is backbone A with insert 2 and the SV40 origin of replication. Plasmid pA2ori− is backbone A with insert 1 without the SV40 origin of replication. Additionally, either pA2ori+ or pA2ori− may include integrase yielding pA2ori+int+ and pA2ori−int+, respectively. Plasmids pA2ori+, pA2ori−, pA2ori+int+ and pA2ori−int+ may be further modified by functionally deleing the reverse transcriptase (RT) gene yielding pA2ori+RT−, pA2ori−RT−, pA2ori+int+RT− and pA2ori−int+RT−, respectively.

In some embodiments, backbone B is used with insert 1. Such constructs optionally the SV40 origin of replication. Plasmid pB1ori+ is backbone B with insert 1 and the SV40 origin of replication. Plasmid pB1ori− is backbone B with insert 1 without the SV40 origin of replication. Additionally, either pB1ori+ or pB1ori− may include integrase yielding pB1ori+int+ and pB1ori−int+, respectively. Plasmids pB1ori+, pB1ori−, pB1ori+int+ and pB1ori−int+ may be further modified by functionally deleting the reverse transcriptase (RT) gene yielding pB1ori+RT−, pB1ori−RT−, pB1ori+int+RT− and pB1ori−int+RT−, respectively.

In some embodiments, backbone B is used with insert 2. Such constructs optionally the SV40 origin of replication. Plasmid pB2ori+ is backbone B with insert 2 and the SV40 origin of replication. Plasmid pB2ori− is backbone B with insert 1 without the SV40 origin of replication. Additionally, either pB2ori+ or pB2ori− may include integrase yielding pB2ori+int+ and pB2ori−int+, respectively. Plasmids pB2ori+, pB2ori−, pB2ori+int+ and pB2ori−int+ may be further modified by functionally deleing the reverse transcriptase (RT) gene yielding pB2ori+RT−, pB2ori−RT−, pB2ori+int+RT− and pB2ori−int+RT−, respectively.

In some embodiments, backbone A minus rev is used with insert 3. Such constructs optionally the SV40 origin of replication. Plasmid pA/r−3ori+ is backbone A with insert 2 and the SV40 origin of replication. Plasmid pA/r−3ori− is backbone A minus rev with insert 3 without the SV40 origin of replication. Additionally, either pA/r−3ori+ or pA/r−3ori− may include integrase yielding pA/r−3ori+int+ and pA/r−3ori−int+, respectively. Plasmids pA/r−3ori+, pA/r−3ori−, pA/r−3ori+int+ and pA/r−3ori−int+ may be further modified by functionally deleing the reverse transcriptase (RT) gene yielding pA/r−3ori+RT−, pA/r−3ori−RT−, pA/r−3ori+int+RT− and pA/r−3ori−int+RT−, respectively.

In some embodiments, backbone C is used with insert 1. Such constructs optionally the SV40 origin of replication. Plasmid pC1ori+ is backbone C with insert 1 and the SV40 origin of replication. Plasmid pC1ori− is backbone C with insert 1 without the SV40 origin of replication. Additionally, either pC1ori+ or pC1ori− may include integrase yielding pC1ori+int+ and pC1ori−int+, respectively. Plasmids pC1ori+, pC1ori−, pC1ori+int+ and pC1ori−int+ may be further modified by functionally deleing the reverse transcriptase (RT) gene yielding pC1ori+RT−, pC1ori−RT−, pC1ori+int+RT− and pC1ori−int+RT−, respectively.

In some embodiments, backbone C is used with insert 2. Such constructs optionally the SV40 origin of replication. Plasmid pC2ori+ is backbone C with insert 2 and the SV40 origin of replication. Plasmid pC2ori− is backbone C with insert 2 without the SV40 origin of replication. Additionally, either pC2ori+ or pC2ori− may include integrase yielding pC2ori+int+ and pC2ori−int+, respectively. Plasmids pC2ori+, pC2ori−, pC2ori+int+ and pC2ori−int+ may be further modified by functionally deleing the reverse transcriptase (RT) gene yielding pC2ori+RT−, pC2ori−RT−, pC2ori+int+RT− and pC2ori−int+RT−, respectively.

In some embodiments, backbone C is used with insert 3. Such constructs optionally the SV40 origin of replication. Plasmid pC3ori+ is backbone C with insert 3 and the SV40 origin of replication. Plasmid pC3ori− is backbone C with insert 3 without the SV40 origin of replication. Additionally, either pC3ori+ or pC3ori− may include integrase yielding pC3ori+int+ and pC3ori−int+, respectively. Plasmids pC3ori+, pC3ori−, pC3ori+int+ and pC3ori−int− may be further modified by functionally deleing the reverse transcriptase (RT) gene yielding pC3ori+RT−, pC3ori−RT−, pC3ori+int+RT− and pC3ori−int+RT−, respectively.

In some embodiments, backbone D is used with insert 4. Such constructs optionally the SV40 origin of replication. Plasmid pD4ori+ is backbone D with insert 4 and the SV40 origin of replication. Plasmid pD4ori− is backbone D with insert 4 without the SV40 origin of replication.

Example 37

In some embodiments, a single expression unit/single inoculant genetic vaccine is provided which comprises a genetic construct that includes a coding sequence which encodes a peptide that has at least one epitope which is an identical to or substantially similar to epitopes of HIV proteins. The coding sequence is under the regulatory control of the CMV immediate early promoter and the SV40 minor polyadenylation signal.

In some embodiments, a single expression unit/single inoculant genetic vaccine is provided which comprises a genetic construct that includes a coding sequence which encodes at least one HIV protein or a fragment thereof. The coding sequence is under the regulatory control of the CMV immediate early promoter and the SV40 minor polyadenylation signal. The HIV protein is selected from the group consisting of gag, pol, env and rev. In some embodiments it is preferred that the genetic vaccine is provided which comprises a genetic construct that includes a coding sequence which encodes at least two HIV proteins or a fragments thereof selected from the group consisting of gag, pol, env and rev or fragments thereof. In some embodiments, it is preferred that the genetic vaccine is provided which comprises a genetic construct that includes a coding sequence which encodes at least three HIV proteins or a fragments thereof selected from the group consisting of gag, pol, env and rev or fragments thereof. In some embodiments, it is preferred that the genetic vaccine is provided which comprises a genetic construct that includes a coding sequence which encodes gag, pol, env and rev or fragments thereof.

In some embodiments, a dual expression unit/single inoculant genetic vaccine is provided which comprises a genetic construct that includes two expression units each of which comprises a coding sequence which encodes a peptide that has at least one epitope which is an identical to or substantially similar to epitopes of HIV proteins. The coding sequence is under the regulatory control of the CMV immediate early promoter and the SV40 minor polyadenylation signal. The two expression units are encoded in opposite directions of each other.

In some embodiments, a dual expression unit/single inoculant genetic vaccine is provided which comprises a genetic construct that includes two expression units each of which comprises a coding sequence which encodes at least one HIV protein or a fragment thereof. Each expression unit comprises a coding sequence that is under the regulatory control of the CMV immediate early promoter and the SV40 minor polyadenylation signal. The HIV protein is selected from the group consisting of gag, pol, env and rev. In some embodiments it is preferred that the genetic vaccine is provided which comprises a genetic construct that includes two expression units, at least one of which comprises a coding which encodes at least two HIV proteins or a fragments thereof selected from the group consisting of gag, pol, env and rev or fragments thereof and the other comprises at least one HIV proteins or a fragments thereof selected from the group consisting of gag, pol, env and rev or fragments thereof. In some embodiments, it is preferred that the genetic vaccine is provided which comprises a genetic construct that includes two expression units, at least one of which comprises a coding sequence which encodes at least three HIV proteins or a fragments thereof selected from the group consisting of gag, pol, env and rev or fragments thereof and the other comprises at least one HIV proteins or a fragments thereof selected from the group consisting of gag, pol, env and rev or fragments thereof. In some embodiments, it is preferred that the genetic vaccine is provided which comprises a genetic construct that comprises two expression units and includes a coding sequence which encodes gag, pol, env and rev or fragments thereof.

Example 38

A genetic construct, plasmid pCMN160Δ16 was made for use in an anti-HIV pharmaceutical kit or pharmaceutical composition. pCMN160Δ16 was constructed as follows:

Step 1: Primers SEQ ID NO:31 and SEQ ID NO:30 were used a PCR fragment from HIV/MN genomic DNA.

Step 2: Primers SEQ ID NO:29 and SEQ ID NO:32 were used a PCR fragment from HIV/MN genomic DNA.

Step 3: Primers SEQ ID NO:31 and SEQ ID NO:32 were combined with 2 μl of reaction material from Steps 1 and 2.

Step 4: Reaction product from Step 3 was cut with Not1 and Mlu1 and inserted into Backbone A described in Example 36 cut with Not1 and Mlu1.

Plasmid pCMN160Δ16 is thereby formed which contains as an insert to Backbone A a coding region which encodes the MN strain ENV Protein with the rev region and half of nef having HLA-DB region changes to HIV-2.

Example 39

The plasmid pGAGPOL.rev2 was made as follows. First the backbone was made. Then an insert with HIV gag and pol was generated and inserted into the backbone.

The backbone was prepared as follows.

Step 1. Digest pMAMneo (Clonetech) with Bgl1. Fill-in with Klenow fragment of Polymerase I. Cut with HindIII. Gel purify 1763 bp fragment.

Step 2. Amplify $Kan^R$ gene from plasmid $pJ4\Omega kan^+$ (Kanmycin resistance gene obtained from Pharmacia Inc. cloned into pJ4Ω obtained as a gift from the Imperial Cancer Research Fund UK; pJ4Ω was originally constructed and reported by Morgenstern, J. P. and H. Land, *Nucl. Acids Res.* 18(4):1068, which is incorporated herein by reference) with oligos SEQ ID NO:33 and SEQ ID NO:34. Blunt off PCR product. Cut with HindIII. Gel purify PCR fragment.

Step 3. Ligate the vector backbone generated from pMAMneo and described in step #1 with the PCR product encoding the $Kan^R$ gene and described in step #2. Isolate plasmid containing the KanR gene and the bacterial origin of replication.

Step 4. Digest resulting plasmid with MluI, fill-in with Klenow fragment of DNA polymerase I. Ligate with SacII linker (New England Biolabs).

Step 5. Digest plasmid obtained in step 4 with AseI and SspI.

Step 6. PCR part of the $Kan^R$ gene from the plasmid described in step 3 using primers SEQ ID NO:35 and SEQ ID NO:36. Cut PCR product with SspI and AseI.

Step 7. Ligate largest fragment obtained in step 5 with PCR product obtained in step 6.

Step 8. Cut ligation product/plasmid obtained in step 7 with HindIII. Blunt off with the Klenow fragment of DNA polymerase I.

Step 9. Cut pCEP4 (Invitrogen) with SalI to release a DNA fragment containing the CMV promoter, polylinker, and SV40 poly A site. Purify this fragment and blunt-off with the Klenow fragment of DNA Polymerase I.

Step 10. Ligate the plasmid obtained in step 8 and the fragment obtained in step 9. Isolate plasmid containing the bacterial origin of replication, the $Kan^R$ gene, the RSV enhancer, the CMV promoter, polylinker, and the SV40 poly A site.

Step 11. Cut plasmid obtained in step 10 with BamHI and NheI.

Step 12. Anneal oligonucleotides SEQ ID NO:37 and SEQ ID NO:38.

Step 13. Ligate the plasmid obtained in step 10 with the annealed oligonucleotides obtained in step 12. Isolate plasmid containing the adapter contained in step 12.

Step 14. Digest plasmid obtained in step 13 with SalI and MluI.

Step 15. PCR amplify the rev open reading frame using BBG35 (RD Systems Inc. Minneapolis, Minn.; which contains the coding region for rev from HIV strain HX3B in pUC19) as a template and primers SEQ ID NO:39 and SEQ ID NO:40. Digest the PCR product with SalI and MluI.

Step 16. Ligate the plasmid obtained in step 14 with the PCR product produced in step 15. Isolate plasmid containing the rev coding region.

Preparation of Gag/Pol Insert.

Step 1. A subclone of part of the HIV-I (HXB2) genome that was cloned into Bluescript (Stratagene). The subclone of HIV-1 contains the complete 5'LTR and the rest of the HIV-1 genome to nucleotide 5795 (Genbank numbering) cloned into the XbaI and SalI sites of Bluescript. The HIV-1 sequences are obtained from the HXB2D plasmid (AIDS Repository).

Step 2. PCR part of the gag coding region from the open reading frame of the plasmid described in step 1 (the subclone of part of the HIV-1 HXB2 genome that is cloned into Bluescript) using primers SEQ ID NO:41 and SEQ ID NO:42.

Step 3. Digest plasmid described in step 1 (the subclone of part of the HIV-1 HXB2 genome that is cloned into Bluescript) with EcoRI. Purify the plasmid that contains the pBluescript backbone, the 5' HIV-1 LTR, the gag coding region and part of the pol coding region and religate.

Step 4. Cut the plasmid obtained in step 3 with NotI and SpeI and ligate with the PCR fragment described in Step 2 after it is digested with NotI and SpeI. Isolate plasmid that contain the PCR fragment instead of the original NotI/SpeI fragment which contains the 5' HIV-1 LTR.

Step 5. Digest the plasmid obtained in step 4 with EcoR1 and SalI.

Step 6. Anneal oligonucleotides SEQ ID NO:43 and SEQ ID NO:44.

Step 7. Ligate the plasmid obtained in step 5 with the adapter obtained in step 6. Isolate plasmid containing the adapter cloned into the EcoRI/SalI sites.

Step 8. Digest the plasmid obtained in step 7 with NdeI and EcoRI.

Step 9. PCR amplify the Rev Response Element (RRE) from a plasmid containing the RRE sequence from HIV-1 strain HXB2 using primers SEQ ID NO:45 and SEQ ID NO:46. Digest the PCR product with NdeI and EcoRI.

Step 10. Ligate the plasmid obtained in step 8 with the PCR product obtained in step 9. Isolate plasmid containing the insert with the RRE sequence.

Step 11. Digest the plasmid obtained in step 10 with NotI and SalI and isolate the fragment containing the gag coding region, the modified pol coding region, and the RRE sequence.

Step 12. Digest the plasmid obtained in step 16 of the protocol for preparing the backbone which is described above with NotI and SalI.

Step 13. Ligate the plasmid obtained in step 12 with the insert obtained in step 11. Isolate plasmids that contain the insert containing the gag coding region, the modified pol coding region, and the RRE sequence.

Step 14. Digest plasmid obtained in step 13 with XbaI and NheI, Blunt-off ends and religate. Isolate the plasmid that is lacking the KpnI site that is present between the XbaI and NheI sites in the plasmid obtained in step 13.

Step 15. Digest the plasmid obtained in step 14 with KpnI and isolate the largest fragment.

Step 16. Anneal oligonucelotides SEQ ID NO:47 and SEQ ID NO:48.

Step 17. Ligate the purified plasmid fragment obtained in step 15 with the adapter obtained in step 16. Isolate plasmid containing the adapter inserted at the KpnI site of the plasmid obtained in step 15.

Example 40

Genetic Immunization with Genes for Regulatory Proteins

Part of the difficulty of combatting HIV arises from the extraordinary variability of the virus and its ability to quickly mutate into new forms. Not only is there substantial protein sequence variation among HIV isolates found in the human population as a whole, but the virus mutates so quickly that every HIV-infected individual actually harbors a number of related HIV microvariants. Such HIV isolates exhibit differences in replication efficiency, tropism, susceptibility to neutralization, and drug resistance. As drug-resistant mutants appear, the benefits of drug therapy fade. With AZT, drug resistance typically arises within the first year of therapy. This constant generation of escape mutants may play a part in the ability of HIV to finally overwhelm host defenses after a long period in which the virus appears to be held in check.

This mutational drift has been reported in various regions of the gp120 envelope glycoprotein, including the principal neutralizing domain of the V3 loop, and in the HIV core proteins as well. HIV regulatory proteins are much more highly conserved than the structural proteins and also exhibit less mutational drift over time. Regulatory proteins therefore present attractive targets for antiviral attack.

HIV exhibits a remarkable temporal regulation of expression of regulatory vs structural proteins. In the early phase of viral replication, mRNAs encoding the regulatory proteins Tat, Rev and Nef predominate, whereas in the late phase, there is greater expression of mRNAs encoding structural proteins, including Gag, Pol, and Env precursors, and many accessory proteins. This shift from early to late phase is triggered when the Rev protein reaches a particular level. The predominance of Tat, Rev and Nef early in the viral replication cycle also makes these proteins favorable targets for antiviral attack. This is especially true for tat and rev, which play absolutely essential roles in transcriptional and post-translational regulation of HIV gene expression, and predominate early in the viral replication cycle, before transcription of viral structural proteins and production of infectious viral particles.

In contrast to tat and rev, which clearly play essential roles in HIV replication, other regulatory proteins such as nef, vpr, vif, and vpu are sometimes referred to as "accessory" proteins. Their functions are less well understood, and the degree to which viral replication is attenuated by loss of a particular function varies considerably and may depend on the host cell being infected. Nevertheless, the strong conservation of such functions among widely diverse HIV isolates, as well as other primate immunodeficiency viruses, suggests the importance of these "accessory" functions in the natural infection process. (See in general, Terwilliger, E. F., (1992) *AIDS Research Reviews* 2:3–27, W. C. Koff, F. Wong-Staal, and R. C. Kennedy, eds. (New York:Marcel Dekker, Inc.). In fact, primate recombinant viruses deleted in either vpr, nef or vif are non-pathogenic in vivo, further demonstrating the importance of these accessory genes in the life cycle of the virus.

There is some evidence that higher level, more protective immune responses against HIV could be achieved by presenting a select few regulatory and/or enzymatic proteins, rather than the entire complement of HIV genes. Accordingly, a focused immunization strategy may desirably involve genetic immunization using coding sequences for one or more regulatory, non-structural HIV proteins, including tat, rev, vpr, nef, vpu or vif. Only vpr has been found to be associated with viral particles, whereas other regulatory proteins, including tat, rev, nef, vif and vpu, are not virion associated.

In some embodiments of genetic immunization against HIV using regulatory genes, the one or more of tat, rev, nef, vif and vpu genes are inserted into backbone A which is described in Example 37. It is preferred that tat and/or rev is used. In some embodiments, tat or rev are inserted into backbone A which is described in Example 37. In some embodiments, Next in descending order of desirability as targets are nef, vpr, vif, and vpu. Preferably, more than one regulatory gene will be employed, including tat and rev; tat, rev, and nef; tat, rev, nef, and vpr; tat, rev, nef, vpr, and vif; tat, rev, nef, vpr, vif, and vpu; as well as combinations thereof; and, optionally, such additional regulatory genes as tev.

The Tat protein is a transactivator of LTR-directed gene expression. It is absolutely essential for HIV replication. Tat is produced early in the viral replication cycle and functional Tat is required for expression of Gag, Pol, Env and Vpr. The predominant form of Tat is an 86-amino acid protein derived from two exon mRNAs. The amino-terminal 58 amino acids are sufficient for transactivation, although with reduced activity. Tat acts on a cis-acting sequence termed tar, to produce a dramatic increase in LTR-driven gene expression. Tat may act in part through increased RNA synthesis and in part by increasing the amount of protein synthesized per RNA transcript. Until recently, Tat was thought to act only on the HIV-1 LTR. However, Tat-activated expression from the JC virus late promoter has also been reported. Tat may also stimulate cell proliferation as an exogenous factor, and may play a contributory role in promoting the growth of Kaposi's Sarcoma in HIV-infected individuals.

Because of such potentially detrimental effects in both HIV-infected and -noninfected individuals, preferred tat constructs employed for genetic immunization are modified to express only non-functional Tat. Mutations capable of inactivating Tat or Rev can in addition act as transdominant mutations, thereby potentially inactivating any functional Tat being produced in an HIV-infected individual.

Rev is a second regulatory protein of HIV that is essential for viral replication. It is a 19 kD (116 amino acid) protein which is expressed from two coding exons found in a variety of multiply spliced mRNAs. Two distinct domains have been identified, a basic region involved in binding to RRE (Rev-response-element)containing transcripts and an "activation" domain that induces nuclear exports of such transcripts as a result of binding. In the course of natural viral infection, Rev is required for expression of the HIV structural proteins Gag, Pol, and Env, as well as Vpr.

Vpr is a 15 kD protein (96 amino acids) in most HIV-1 strains, although the Vpr open reading frame is extensively truncated in many viral strains extensively passaged in cell culture. The vpr open reading frame is also present in HIV-2 and most SIV isolates. Vpr is the first retroviral regulatory protein found to be associated with HIV viral particles. Its presence in the HIV virion suggests it may serve a function at some early point in the viral replication cycle. Vpr accelerates HIV replication, especially early in infection. Vpr increases the level of expression of reporter genes linked to the HIV LTR by about three fold. Moreover, Vpr and Tat appear to act synergistically with respect to LTR-linked genes. Vpr can be isolated from the serum of HIV-infected individuals and appears to increase the ability of the virus to infect new cells. Vpr has also been found to inhibit cell proliferations and to induce cell differentiation (Levy, D. N. et al., *Cell* (1993) 72:1–20), a finding that may be significant in view of reports that primary monocyte/macrophages are infectible in vitro only while undergoing differentiation (Schuitemaker, H. et al., (1992) *J. Clin. Invest.* 89:1154–1160. Even cells that are unable to support HIV replication may be disregulated by the effects of Vpr. For example, Vpr may be responsible for the muscle wasting frequently observed in AIDS patients. Because of the potentially detrimental activity of Vpr, genetic immunization should preferably be carried out with a modified vpr construct which will express a non-functional Vpr protein.

Nef (also called 3' orf in older literature) is a 25–27 kD protein. It has been suggested that Nef may be involved in the downregulation of CD4+ T lymphocytes. In addition, Nef may play a role in cell signaling. Nef appears to be important for the establishment of HIV infection in vivo. Nef-specific CTLs are believed to be important in controlling HIV infection in vivo.

Vif is a 23 kD cytoplasmic protein designated "viral infectivity factor". Although Vif-defective mutant viruses are not compromised with respect to cell-to-cell transmission, they exhibit a profound decrease in ability to infect many CD4+ cell lines. Without Vif, there is decreased budding of virus, and decreased infectivity. In primate studies, Vif deletion mutants exhibit a severely diminished ability to establish infection in vivo. These studies support a clinical role for Vif in virus replication in the host.

Vpu is a 15–20 kD (81 amino acid) protein. Although Vpu(+) and Vpu(-) viruses produce the same amount of viral protein, the latter exhibit increased intracellular accumulation of viral proteins together with decreased extracellular virus. This suggests that Vpu may be involved in the assembly and/or release of viral particles.

Simple retroviruses, such as murine and avian viruses, lack proteins analogous to the HIV-1, HIV-2, and SIV regulatory proteins. In such animals retroviral infection tends to be self-limiting, with clearance of virus and decreased pathogenicity. Similarly, HTLV-1, which includes only Tax (which acts much like Tat and also exhibits vpr-like activity) and Rex (which acts much like Rev) is cleared in many individuals. Genetic immunization with regulatory genes is considered relevant not only for HIV, but also for viruses such as HBV (X gene product) and HCV, and HTLV-1 (Tax) and (Rex). In all of these viruses the regulatory genes are believed to play a critical role in the virus life cycle and the establishment of infection.

Example 41

Construction of HIV-1 Regulatory Plasmid, pREG

The pREG plasmid is constructed in a stepwise fashion, and each intermediate can be tested for protein expression before construction is continued. An expression vector supporting the expression of tat and rev is constructed via two steps. First, an amplification product containing a 5' NheI site, the HIV-1 major splice donor site, the majority of the tat coding region, the region encoding the amino terminal region of the rev protein and an AvaII site is amplified from a synthetic template. This synthetic template is generated using the published sequences of HXB2 strain of HIV-1 obtained from the GenBank Database, and is altered to mutate the cysteine residues at positions 22 and 30 of the tat protein. These mutations have been shown to render tat non-functional (Kuppuswamy, et al. (1989) *Nucleic Acids Research* 17(9): 3551–3561).

The PCR product is ligated into a vector that is digested with NheI and AvaII and which contains a kanamycin resistance gene and a pBR322 origin of replication. In addition, this plasmid contains a cytomegalovirus promoter, a Rous sarcoma virus enhancer, the rev coding region and a SV40 polyadenylation signal. The rev sequence present in the plasmid is derived from the proviral clone of HIV-1 III$_B$. This will generate an expression vector containing a complete, but mutated, tat coding region and a complete rev coding region.

The subsequent step is performed to generate a PCR product containing an AvaII site at its 5' end, a mutation at amino acid position 81 of rev, approximately 30% of the rev coding region, approximately 30% of the nef coding region, and a MluI site at the 3' end. The amino acid change at position 81 has been shown to eliminate rev function, and therefore, the resulting plasmid will lead to production of non-functional rev protein (Bogard, H. and Greene, W. C. (1993) *J. Virol.* 67(5):2496–2502). It is assumed that the major deletion of the nef coding region will result in production of a non-functional nef protein. The 5' AvaII site and the mutation at amino acid position 81 of the rev protein are introduced on the 5' PCR primer which is complementary to the coding region of rev containing both the AvaII site and the nucleotide encoding amino acid 81. A stop codon causing termination of Nef at amino acid position 63 and the 3' coding cloning site, MluI, will be introduced by the 3' PCR primer. The template for this PCR amplification is a plasmid or synthetic template containing the rev and nef coding regions from the MN strain of HIV-1. The resulting PCR product will be digested with AvaII and MluI, and used to replace the smaller AvaII-MluI fragment which results after digestion of the tat-rev plasmid described in the preceding paragraph with AvaII and MluI.

Optionally, vpr can be added to this plasmid in one of two sites. In one approach, vpr can be amplified using a 5' PCR primer containing MluI site upstream of sequences which span the vpr translational start codon and a 3' PCR primer complementary to the vpr stop codon and sequences that flank it which also contain a MluI cloning site. Sequences upstream of the start codon contain a splice acceptor. The PCR product can be digested with MluI and inserted into the tat rev nef plasmid described above after its digestion with MluI.

Alternatively, the vpr amplification can be performed in analogous manner, however, the PCR primers would contain restriction sites compatible with cloning into another vector so that it is expressed under the control of a second eukaryotic promoter. The cassette derived from this plasmid, containing the second promoter followed by the vpr coding region, followed by the a polyA sequence, could be released by digestion with restriction enzymes that flank the cassette, but do not cut within it. The resulting DNA fragment would be cloned into a unique site of the tat, rev, vpr plasmid that falls outside of the region necessary for the expression of tat rev vpr. In this way, a plasmid having two expression units is formed.

Example 42

Construction of HCV and HTLV-1 Plasmids

A similar approach can be used to generate a plasmid expressing HTLV-1 or HCV encoded proteins having enzymatic functions required for the viral life cycle and/or for the regulatory proteins of these viruses. For HTLV-1, a plasmid encoding the regulatory protein, TAX, is generated using the a plasmid backbone and a cloning strategy similar to those described above. Such HCV genes that encode enzymatic proteins include the RNA-dependent RNA-polymerase, a protein having helicase/protease function. The sequences necessary are published and available through GenBank. The viral organization of HTLV-1 and HCV are published in Cann, A. J. and Chen, I. S. Y. *Virology* 2nd Edition, edited by B. N. Fiddr, Raven Press, Ltd., New York, 1990 and Bradley, D. W. *Transfusion Medicine Reviews*, 1(2):93–102, 1992, respectively.

Example 43

Genetic Immunization with Enzymatic Genes

Genetic immunization with genes encoding proteins with enzymatic functions, such as the HIV pol gene can also be an important antiviral strategy since enzymes such as Pol are necessary for the production of live virus. Without polymerase or any of its component functions, HIV is non-pathogenic and non-infectious. Similarly, the enzymatic genes of other viruses, such as the HBV polymerase, are attractive targets for genetic immunization. See, e.g., Radziwill et al., Mutational Analysis of the Hepatitis B Virus P Gene Product: Domain Structure and RNase H Activity, *J. Virol.* 64 (2): 613–620 (1990).

One reason for the attractiveness of viral enzymes as an immunological target is the limited ability of such enzymes to mutate their amino acid sequence and still maintain their enzymatic functions. For example, with HIV-1, Pol exhibits a limited number of "escape" mutations that are associated with resistance to nucleotide analogs such as AZT. However, the vast majority of immunological targets within the protein are preserved even in the drug escape mutants.

Example 44

Construction of HBV Polymerase Plasmid

Experiments reported in the literature indicate that HBV polymerase expression has been achieved in tissue culture cells when both the core and polymerase open reading frames are present in a mRNA molecule. It has also been demonstrated that in this situation, mutation of the core ATG did not influence polymerase expression.

The HBV genome is amplified from a plasmid containing a head-to-tail dimer of the ADW HBV strain. Because expression of polymerase only, and not core is desired, the 5' PCR primer is designed to mutate the precore and core translation initiation codons. In addition, this primer also introduces a mutant DR1 sequence to eliminate the possibility of the generation of a replication-competent HBV genomic RNA. This PCR product is placed into a plasmid containing a kanamycin resistance gene and a pBR322 origin of replication. In addition, this plasmid contains a cytomegalovirus promoter, a Rous sarcoma virus enhancer, and a SV40 polyadenylation signal. The translation initiation codons for surface antigen and the product of the X coding region are mutated to prevent the expression of the HBS and X gene products.

According to another approach to achieve expression of the HBV polymerase, a PCR product encoding the entire polymerase coding region is amplified and cloned into a vector containing a kanamycin resistance gene and a pBR322 origin of replication. In addition, this plasmid contains a cytomegalovirus promoter, a Rous sarcoma virus enhancer, and a SV40 polyadenylation signal. The 5' PCR primer for this amplification contains a cloning site and spans the translational initiation codon of the polymerase gene. The 3' PCR product contains a restriction site for cloning the insert into the expression vector and also is complementary to the traditional stop codon of the HBV polymerase gene and sequences that flank this stop codon. After ligation of this PCR product into a plasmid containing the kanamycin resistance gene, a pBR322 origin of replication, a cytomegalovirus promoter, a Rous sarcoma virus enhancer, and a SV40 polyadenylation signal, the translation initiation codons for the Hepatitis B surface antigen and X genes are mutated to prevent expression of these gene products. An alternative strategy is used similar to that described above, however, the 3' PCR primer in this case includes the HBVpolyA signal and sequences which flank this signal. This 3' primer is used in the case that sequences including and/or surrounding the HBV polyA signal are important for expression. A mutational analysis has demonstrated that the function of the HBV polymerase gene product can be eliminated by particular nucleotide changes (Radziwell, G. et al. (1990) *J. Virol.* 64(2):613–620). Before utilizing a plasmid constructed as described above, the expressed polymerase can be mutated by the introduction of one of these mutations or others that are analogous.

Example 45

Granulocyte-macrophage colony stimulating factor (GM-CSF) exhibits stimulatory effects on a variety of cell lineages including neutrophils, monocyte/macrophages and eosinophils. The effects of GM-CSF make it an attractive therapeutic model. GM-CSF has been approved by the FDA for use in the autologous bone marrow transplantation and clinical trials have been initiated to test the efficacy in the treatment of various neutropenias. Presently, GM-CSF is administered as a protein which usually requires that it be administered in multiple doses. Proteins must be produced and purified.

An alternative approach to the use of GM-CSF protein is the direct administration of a gene construct which contains a gene encoding GM-CSF in conjunction with the administration of . . . . The genetic construct is constructed by PCR of a GM-CSF gene including signal sequence. The genetic construct preferably contains a kanamycin resistance gene (aminoglycoside 3'-phosphotransferase gene), a bacterial origin of replication, sequences that support expression of the GM-CSF coding region in the cells that the plasmid is introduced into such as the vectors described as backbones in Example 36. The plasmid preferably contains a mammalian origin of replication induced by the cellular replication associated with . . . administration. If the EBV origin of replication is used, the sequence that encodes the nuclear antigen EBNA-1 is also included with the appropriate regulatory sequences. The primers for PCR amplification of the insert contain restriction enzyme sites to allow cloning into the expression vector and are complementary to the 5' and 3' ends of the GM-CSF coding sequences. The PCR reaction is performed with a cDNA clone as described in Lee et al. *Proc. Natl. Acad. Sci., USA* 82:4360–4364.

Example 46

Chronic myelogenous leukemia (CML) is a clonal myeloproliferative disorder of the hematopoietic stem cells associated with the Philadelphia chromosome; a chromosome abnormality resulting from translocation between chromosomes 9 and 22. The breakpoints on chromosome 22 are clustered in a 6 kb region termed the breakpoint cluster region (BCR), while on chromosome 9, the breakpoints are scattered throughout a 90 kb region upstream from c-abl exon 2. The various 9:22 translocations that result can be subdivided into two types: K28 translocations and L6 translocations. Transcription through the bcr-abl translocation results in the generation of fusion mRNAs. Antisense targeted to the bcr-abl junction of the mRNAs has been demonstrated to decrease the ability of hematopoietic cells obtained from CML patients to form colonies.

Example 47

Gene constructs useful in pharmaceutical kits and compositions for vaccination against and treatment for HBV are constructed with vectors described as backbones in Example 36. The plasmids contain HBV structural genes, particularly genes that encode HBV surface antigen and/or HBV core antigen core and/or HBV precore antigen.

Example 48

Gene constructs useful in pharmaceutical kits and compositions for vaccination against and treatment for HCV are constructed with vectors described as backbones in Example 36. The plasmids contain HCV structural genes, particularly genes that encode HCV core protein and/or HCV envelope protein.

Example 49

The gene construct PREV was designed which contains a nucleotide sequence that encodes HIV rev as the sole target protein. The coding sequence of rev is cloned into Backbone A described in Example 36 from BBG35 (RD Sytems Inc. Minneapolis, Minn.) which contains the coding region of rev from HIV strain HX3B in pUC19.

TABLE 1

| | |
|---|---|
| Picornavirus Family | |
| Genera: | Rhinoviruses: (Medical) responsible for ~50% cases of the common cold. Etheroviruses: (Medical) includes polioviruses, coxsackieviruses echoviruses, and human enteroviruses such as hepatitis A virus. Apthoviruses: (Veterinary) these are the foot and mouth disease viruses. |
| Target antigens: | VP1, VP2, VP3, VP4, VPG |
| Calcivirus Family | |
| Genera: | Norwalk Group of Viruses: (Medical) these viruses are an important causative agent of epidemic gastroenteritis. |
| Togavirus Family | |
| Genera: | Alphaviruses: (Medical and Veterinary) examples include Senilis viruses, RossRiver virus and Eastern & Western Equine encephalitis. Reovirus: (Medical) Rubella virus. |
| Flariviridue Family | |
| | Examples include: (Medical) dengue, yellow fever, Japanese encephalitis, St. Louis encephalitis and tick borne encephalitis viruses. |
| Hepatitis C Virus: | (Medical) these viruses are not placed in a family yet but are believed to be either a togavirus or a flavivirus. Most similarity is with togavirus family. |
| Coronavirus Family: | (Medical and Veterinary) Infectious bronchitis virus (poultry) Porcine transmissible gastroenteric virus (pig) Porcine hemagglutinating encephalomyelitis virus (pig) Feline infectious peritonitis virus (cats) Feline enteric coronavirus (cat) Canine coronavirus (dog) The human respiratory coronaviruses cause ~40 cases of common cold. EX. 224E, OC43 Note - coronaviruses may cause non-A, B or C hepatitis |
| Target antigens: | E1 - also called M or matrix protein E2 - also called S or Spike protein E3 - also called HE or hemagglutin-elterose glycoprotein (not present in all coronaviruses) N - nucleocapsid |
| Rhabdovirus Family | |
| Genera: | Vesiliovirus Lyssavirus: (medical and veterinary) rabies |
| Target antigen: | G protein N protein |
| Filoviridue Family: | (Medical) Hemorrhagic fever viruses such as Marburg and Ebola virus |
| Paramyxovirus Family: | |
| Genera: | Paramyxovirus: (Medical and Veterinary) Mumps virus, New Castle disease virus (important pathogen in chickens) Morbillivirus: (Medical and Veterinary) |

TABLE 1-continued

| | |
|---|---|
| | Measles, canine distemper Pneuminvirus: (Medical and Veterinary) Respiratory syncytial virus (Medical) The Influenza virus |
| Orthomyxovirus Family | |
| Bungavirus Family | |
| Genera: | Bungavirus: (Medical) California encephalitis, LA Crosse Phlebovirus: (Medical) Rift Valley Fever Hantavirus: Puremala is a hemahagin fever virus Nairvirus (Veterinary) Nairobi sheep disease Also many unassigned bungaviruses (Medical) |
| Arenavirus Family | LCM, Lassa fever virus |
| Reovirus Family | |
| Genera: | Reovirus: a possible human pathogen Rotavirus: acute gastroenteritis in children Orbiviruses: (Medical and Veterinary) Colorado Tick fever, Lebombo (humans) equine encephalosis, blue tongue |
| Retrovirus Family Sub-Family: | |
| | Oncorivirinal: (Veterinary) (Medical) feline leukemia virus, HTLVI and HTLVII Lentivirinal: (Medical and Veterinary) HIV, feline immunodeficiency virus, equine infections, anemia virus Spumavirinal |
| Papovavirus Family Sub-Family: | |
| | Polyomaviruses: (Medical) BKU and JCU viruses |
| Sub-Family: | |
| | Papillomavirus: (Medical) many viral types associated with cancers or malignant progression of papilloma |
| Adenovirus (Medical) | |
| | EX AD7, ARD., O.B. - cause respiratory disease - some adenoviruses such as 275 cause enteritis |
| Parvovirus Family (Veterinary) | |
| | Feline parvovirus: causes feline enteritis Feline panleucopeniavirus Canine parvovirus Porcine parvovirus |
| Herpesvirus Family | |
| Sub-Family: Genera: | alphaherpesviridue Simplexvirus (Medical) HSVI, HSVII Varicellovirus: (Medical - Veterinary) pseudorabies - varicella zoster |
| Sub-Family - Genera: | betaherpesviridue Cytomegalovirus (Medical) HCMV Muromegalovirus |
| Sub-Family: Genera: | Gammaherpesviridue Lymphocryptovirus (Medical) EBV - (Burkitts lympho) Rhadinovirus |
| Poxvirus Family | |
| Sub-Family: | Chordopoxviridue (Medical - Veterinary) |

TABLE 1-continued

| | |
|---|---|
| Genera: | Variola (Smallpox) Vaccinia (Cowpox) Parapoxivirus - Veterinary Auipoxvirus - Veterinary Capripoxvirus Leporipoxvirus Suipoxvirus |
| Sub-Family: | Entemopoxviridue |
| Hepadnavirus Family | |
| | Hepatitis B virus |
| Unclassified | |
| | Hepatitis delta virus |

TABLE 2

Bacterial pathogens

| | |
|---|---|
| | Pathogenic gram-positive cocci include: pneumococcal; staphylococcal; and streptococcal. Pathogenic gram-negative cocci include: meningococcal; and gonococcal. Pathogenic enteric gram-negative bacilli include: enterobacteriaceae; pseudomonas, acinetobacteria and eikenella; melioidosis; salmonella; shigellosis; hemophilus; chancroid; brucellosis; tularemia; yersinia (pasteurella); streptobacillus moniliformis and spirillum; listeria monocytogenes; erysipelothrix rhusiopathiae; diphtheria; cholera; anthrax; donovanosis (granuloma inguinale); and bartonellosis. Pathogenic anaerobic bacteria include: tetanus; botulism; other clostridia; tuberculosis; leprosy; and other mycobacteria. Pathogenic spirochetal diseases include: syphilis; treponematoses: yaws, pinta and endemic syphilis; and leptospirosis. Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include rickettsial and rickettsioses. Examples of mycoplasma and chlamydial infections include: mycoplasma pneumoniae; lympho-granuloma venereum; psittacosis; and perinatal chlamydial infections. |
| Pathogenic eukaryotes | |
| | Pathogenic protozoans and helminths and infections thereby include: amebiasis; malaria; leishmaniasis; trypanosomiasis; toxoplasmosis; pneumocystis carinii; babesiosis; giardiasis; trichinosis; filariasis; schistosomiasis; nematodes; trematodes or flukes; and cestode (tapeworm) infections. |

What is claimed is:

1. A method of introducing nucleic acid molecules into cells of an individual comprising the step of administering in vivo to cells in said individual's body urea and nucleic acid molecules wherein said nucleic acid molecules are taken up by said cells.

2. The method of claim 1 wherein said nucleic acid molecules are administered to cells in said individual's body cells by intramuscular administration.

3. The method of claim 1 wherein said nucleic acid molecules are DNA molecules.

4. The method of claim 3 wherein said DNA molecules are plasmids.

5. A method of generating an immune response in an individual against an antigen comprising administering in vivo to cells of said individual's body urea and DNA molecules that comprise a DNA sequence that encodes said antigen, said DNA sequence operatively linked to regulatory sequences which control the expression of said DNA sequence; wherein said DNA molecules are taken up by cells, said DNA sequence is expressed in said cells and an immune response is generated against said antigen.

6. The method of claim 5 wherein said DNA molecules are plasmids.

7. The method of claim 5 wherein said DNA molecules are administered to cells in said individual's body cells by intramuscular administration.

8. The method of claim 5 wherein said DNA molecules are administered to cells in said individual's body cells by administration into skin.

9. The method of claim 5 wherein said urea and said DNA molecules are administered simultaneously.

10. The method of claim 5 wherein said antigen is a pathogen antigen.

11. The method of claim 5 wherein said antigen is a protein associated with cells that characterize a disease.

12. The method of claim 10 wherein said pathogen is a virus selected from the group consisting of: human immunodeficiency virus, HIV; human T cell leukemia virus, HTLV; influenza virus; hepatitis A virus, HAV; hepatitis B virus, HBV; hepatitis C virus, HCV; human papilloma virus, HPV; Herpes simplex 1 virus, HSV1; Herpes simplex 2 virus, HSV2; Cytomegalovirus, CMV; Epstein-Barr virus, EBV; rhinovirus; and, coronavirus.

13. The method of claim 11 wherein said disease is characterized by hyperproliferating cells.

14. The method of claim 11 wherein said disease is an autoimmune disease.

15. The method of claim 13 wherein said protein is selected from the group consisting of: protein products of oncogenes, myb, myc, fyn, ras, sarc, neu and trk; protein products of translocation gene bcl/abl; p53; EGRF; variable regions of antibodies made by B cell lymphomas; and variable regions of T cell receptors of T cell lymphomas.

16. The method of claim 14 wherein said protein is selected from the group consisting of: variable regions of antibodies involved in B cell mediated autoimmune disease; and variable regions of T cell receptors involved in T cell mediated autoimmune disease.

17. A pharmaceutical composition comprising urea and DNA molecules that comprise a nuclcotide sequence which encodes a protein wherein said nucleotide sequence is operably linked to regulatory sequences required for expression in a mammal.

18. The pharmaceutical composition of claim 17 wherein said protein is selected from the group consisting of: pathogen antigens, proteins associated with hyperproliferating cells; and proteins associated with cells that characterize an autoimmunc disease.

19. A pharmaceutical kit comprising:

i) a container that comprises DNA molecules that comprise a nucleotide sequence which encodes a protein wherein said nucleotide sequence is operably linked to regulatory sequences required for expression in a mammal; and ii) a container that comprises urea.

20. The pharmaceutical kit of claim 19 wherein said protein is selected from the group consisting of: pathogen antigens, proteins associated with hyperproliferating cells; and proteins associated with cells that characterize an autoimmunc disease.

21. A method of delivering a protein into cells of an individual in vivo comprising administering to cells of said individual's body, urea and DNA molecules that comprise a DNA sequence that encodes said protein, said DNA sequence operatively linked to regulatory sequences which control the expression of said DNA sequence; wherein said DNA molecules are taken up by cells, said DNA sequence is expressed in said cells producing said protein in said cells.

22. The method of claim 21 wherein said DNA molecules are plasmids.

23. The method of claim 21 wherein said DNA molecules are administered to cells in said individual's body cells by intramuscular administration.

24. The method of claim 21 wherein said DNA molecules are administered to cells in said individual's body cells by administration into skin.

* * * * *